United States Patent [19]
Schmitt-Willich et al.

[11] Patent Number: 5,876,698
[45] Date of Patent: Mar. 2, 1999

[54] MACROCYCLIC POLYMER COMPLEXING AGENTS, THEIR COMPLEXES, PROCESS FOR THEIR PRODUCTION AND PHARMACEUTICAL AGENTS CONTAINING THESE COMPOUNDS

[75] Inventors: Heribert Schmitt-Willich; Johannes Platzek; Heinz Gries; Gabriele Schuhmann-Giampieri; Thomas Frenzel, all of Berlin, Germany

[73] Assignee: Schering Aktiengesellschaft, Berlin, Germany

[21] Appl. No.: 881,269

[22] Filed: May 11, 1992

[30] Foreign Application Priority Data

May 10, 1991 [DE] Germany ............... 41 15 789.3

[51] Int. Cl.$^6$ ............ A61K 49/00; G01N 31/00; G01N 33/48

[52] U.S. Cl. ............ 424/9.363; 424/1.11; 424/1.65; 424/9.3; 424/9.4; 424/9.1

[58] Field of Search ............ 540/465, 474; 424/1.53, 1.65, 1.69, 1.73, 9, 1.11, 9.1, 9.3, 9.362, 9.4; 534/15, 16, 10, 14; 530/300, 409

[56] References Cited

U.S. PATENT DOCUMENTS

| | | | |
|---|---|---|---|
| 4,385,046 | 5/1983 | Milbrath | 424/9 X |
| 4,423,158 | 12/1983 | Porath | 536/56 X |
| 4,855,353 | 8/1989 | Kurami et al. | 525/54.1 |
| 4,885,363 | 12/1989 | Tweedle et al. | 540/465 |
| 4,985,233 | 1/1991 | Klaveness et al. | 424/9 |
| 4,986,980 | 1/1991 | Jacobsen | 424/9 |
| 5,198,208 | 3/1993 | Berg et al. | 424/1.1 |
| 5,271,924 | 12/1993 | Hashiguchi et al. | 424/9 |
| 5,277,895 | 1/1994 | Platzek et al. | 424/9 |
| 5,364,613 | 11/1994 | Sieving et al. | 424/9 |
| 5,364,614 | 11/1994 | Platzek et al. | 424/9 |

FOREIGN PATENT DOCUMENTS

| | | |
|---|---|---|
| 186 947 | 7/1986 | European Pat. Off. |
| 233 619 | 8/1987 | European Pat. Off. |
| 255 471 | 2/1988 | European Pat. Off. |
| 414 288 | 2/1991 | European Pat. Off. |
| 454 078 | 10/1991 | European Pat. Off. |
| 457 438 | 11/1991 | European Pat. Off. |
| 90/12050 | 10/1990 | WIPO |
| 91/14186 | 9/1991 | WIPO |

OTHER PUBLICATIONS

Bioconjugate Chemistry, Band 1, Nr. 1, Jan./Feb. 1990, pp. 65–71, American Chemical Society, Wash. D.C.; P.F. Sieving et al: "Preparation & characterization of paramagnetic polychelates and their protein conjugates", p. 65.

"Synthesis & Characterization of the Gadolinium(3+) Complex of DOTA–Propylamide: A Model DOTA–Protein Conjugate"; Sherry et al, Inorganic Chemistry, 1989, 28, 620–622.

Selective Binding of Metal Ions to Macromolecules Using Bifunctional Analogs of EDTA, Sundberg et al, Journal of Medicinal Chemistry, 1974 vol. 17, No. 12, pp. 1304–1307.

"Albumin Labeled with Gd–DTPA as an Intravascular, Blood Pool–Enhancing Agent for MR Imaging: Biodistribution and Imaging Studies", Schmiedl et al, 1985 RSNA annual meeting (Contrast Media Laboratory of the Department of Radiology, Univ. of CA, San Francisco, CA, pp. 205–210.

Search Report in EP 92 25 0110.

Derwent Abtract AN#88–030657 of EP 255,471.

*Primary Examiner*—John Kight
*Assistant Examiner*—Dameron Jones
*Attorney, Agent, or Firm*—Millen, White, Zelano, & Branigan, P.C.

[57] ABSTRACT

Polymeric compounds of general formula I $$(M)_n A \qquad (I)$$

in which

M stands for the radical of a macrocyclic complexing agent,

A stands for a backbone molecule, which shows a deficit of n amino groups, n hydroxy groups or n carboxy groups, n stands for the numbers 1 to 400, characterized in that M, independent of one another, stands for complexing agents of general formula IA

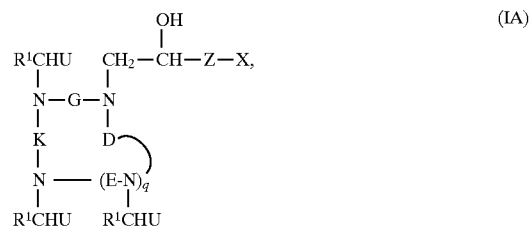

in which all variables are defined herein.

24 Claims, No Drawings

MACROCYCLIC POLYMER COMPLEXING AGENTS, THEIR COMPLEXES, PROCESS FOR THEIR PRODUCTION AND PHARMACEUTICAL AGENTS CONTAINING THESE COMPOUNDS

BACKGROUND OF THE INVENTION

The invention relates to new macrocyclic polymer complexing agents and complexes, agents containing these compounds, the use of the complexes in diagnosis and treatment as well as processes for the production of these compounds and agents.

Magnevist® (GdDTPA/dimeglumine) is the first recorded contrast medium for nuclear spin tomography (MRI= Magnetic Resonance Imaging). It is especially well-suited for the diagnosis of pathological areas (e.g., inflammations, tumors, etc.). The compound is eliminated through the kidneys after intravenous injection; an extrarenal elimination is practically not observed.

A drawback of Magnevist® is that after intravenous administration it is uniformly distributed between the vascular and the interstitial space. Thus, defining the limits of the vessels relative to the surrounding interstitial space when using Magnevist® is not possible.

A contrast medium which is distributed exclusively in the vascular space (vessel space) would be desirable especially for the representation of vessels. Such a blood-pool agent is to make it possible to differentiate, with the help of nuclear spin tomography, tissue that is well supplied with blood from tissue poorly supplied with blood and thus to diagnose an ischemia. It would also be possible to differentiate infarcted tissue because of its anemia from the surrounding healthy or ischemic tissue, when a vascular contrast medium is used. This is of special importance if it is, e.g., a matter of differentiating a myocardial infarction from an ischemia.

Therefore, there is a need for contrast media which can label the vascular space (blood-pool agent). These compounds are to be distinguished by a good compatibility and by a high effectiveness (high increase of the signal intensity with MRI).

Macromolecules are generally suitable as contrast media for angiography. But albumin-GdDTPA (Radiology 1987, 162: 205), e.g., in the rat shows a concentration in hepatic tissue, which constitutes almost 30% of the dose, 24 hours after intravenous injection. Further, only 20% of the dose is eliminated within 24 hours.

The macromolecule polylysine-GdDTPA (European patent application, publication no. 0 233 619) proved suitable as blood-pool agent. But it shows the drawback that the openchain complexing agent DTPA in the desired prolonged retention times of the contrast medium in the body does not optionally bind the metal ions. This applies also to the carbohydrate complexes claimed in European patent application 0 186 947, as well as to the macromolecules labeled with radioisotopes described in J. Med. Chem. 1974, Vol. 17, 1304.

Recently, amides of macrocyclic complexing agents for bonding to macromolecules were proposed in PCT WO 90/12050. But, as is generally known, by conversion of one of the carboxy groups of 1,4,7,10-tetraazacyclododecane-tetraacetic acid (DOTA) to an amide group, the stability constant of the gadolinium complex is reduced by four orders of magnitude (A. D. Sherry et al., Inorg. Chem. 1989, 28, 620), so that the problem of cleavage of toxic metal ions from the macromolecular complexes was still not able to be satisfactorily solved in this way.

SUMMARY OF THE INVENTION

Therefore, it is desired to make available macromolecule complexes, which are distributed intravascularly or concentrated specifically, and simultaneously show a high stability relative to the known structures. This is achieved by this invention.

It has now been found that macromolecule complexes, in which a macrocyclic complexing agent is bound not by simply an amide bond but by a β-hydroxyalkyl group-containing moiety, surprisingly show these desired properties.

The invention thus relates to polymeric compounds of general formula I

$$(M)_n A \qquad (I)$$

in which

M stands for the radical of a macrocyclic complexing agent,

A stands for a backbone molecule, having a deficit of m amino groups, m hydroxy groups and/or m carboxy groups which prior to bonding to $(M)_n$ are present in A, n stands for a number 1 to 400, each m independently is 1 to 400, the sum of all m's being equal to n, characterized in that each M, independent of one another, stands for a complexing agent of general formula IA

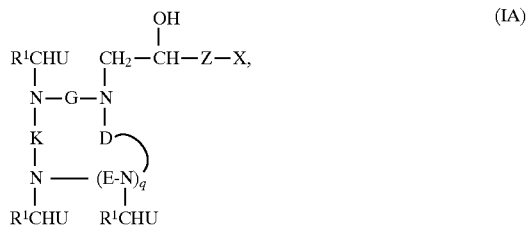

in which

D, E, G, K, can be the same or different and, each stands for the group $-(CH_2)_o-$ with o meaning the numbers 2, 3, 4 or 5 q stands for the numbers 0, 1 or 2, $R^1$ stands for a hydrogen atom or a branched or unbranched $C_1-C_4$ alkyl, phenyl, $C_7-C_{12}$ aralkyl group, U stands for a $CO_2H$ or $PO_3H_2$ group, Z stands for a straight-chain, branched, saturated or unsaturated $C_1-C_{20}$ alkylene group optionally containing imino, phenylene, phenylenoxy, phenylenimino, amide, hydrazide, carbonyl and/or ester group or groups, oxygen, sulfur and/or nitrogen atoms, all optionally substituted when possible by hydroxy, mercapto, oxo, thioxo, carboxy, ester and/or amino group or groups, X stands for $-CONH-$, $-NHCO-$, $-NHCS-$, $-NHCSNH-$, $-NHCONH-$, $-CO_2-$, $-O-$, $-OCO-$, $-COCH_2O-$, $-NR^2CH_2CONH-$, $-NR^2CH_2COO-$, $-OCHR^2CONH-$, $-OCHR^2COO-$ or $-NR-$, R stands for a hydrogen atom or the group $-(CH_2)_pCOOH$ with p meaning the numbers 1–5, and R means a hydrogen atom or a $C_1-C_{20}$ hydrocarbon radical optionally substituted by 1 to 3 carboxy, 1 to 3 sulfonic acid ($SO_3H$), 1 to 5 hydroxy, 1 to 5 $C_1-C_{10}$ alkoxy, 1 to 5 $C_6-C_{10}$ aryloxy, 1 to 5 $C_7-C_{11}$ aralkoxy, 1 to 5 ester (e.g., COOR' where R' is $C_{1-10}$-alkyl, $C_{6-10}$-aryl or $C_{7-11}$-aralkyl) or 1 to 5 amide groups (e.g., CONR"$_2$, where each R" independently is H or an R' group) and/or optionally containing 1 to 3 carbonyl, 1 to 3 ester (as above), 1 to 3 amide (as above), and/or 1 sulfonyl group, and/or 1 to 10 oxygen and/or 1 to 4 nitrogen atoms, or a second radical of formula Ia which can be the same or different as the first radical Ia, their completely or incompletely metalated complexes with the elements of atomic numbers 21–29, 31, 32, 37–39, 42–44, 49, 57–83, as well as their salts.

The complexes according to the invention are suitable because of their signal-transmitting properties and their specific bonding to organs, tissues, tumors and cells in vivo especially to distinguish healthy and diseased tissue in imaging with the help of nuclear spin tomography, x-ray diagnosis and scintigraphy. The complexing agents according to the invention are suitable for detoxifying toxic metal ions and are used as vehicles of metal ions, also of radio-isotopes for radiotherapeutical and diagnostic use in nuclear medicine.

For nuclear resonance and x-ray diagnosis, complexes are suitable which contain ions of an element of atomic numbers 21 to 29, 42, 44 or 57 to 83, as well as optionally cations of inorganic and/or organic bases, amino acids or amino acid amides (e.g., with NR"$_2$). The high number of metal ions often necessary for imaging is achieved by coupling a plurality of macrocyclic complexing agents or complexes to backbone molecules.

If the agent according to the invention is intended for use in NMR diagnosis, the central ion of the complex salt has to be paramagnetic. These are especially the divalent and trivalent ions of elements of atomic numbers 21–29, 42, 44 and 58–70. Suitable ions are, for example, the chromium (III), manganese(II), iron(II), cobalt(II), nickel(II), copper (II), praseodymium(III), neodymium(III), samarium(III) and ytterbium(III) ion. Because of their very great magnetic moment, the gadolinium(III), terbium(III), dysprosium(III), holmium(III), erbium(III) and iron(III) ion are especially preferred.

If the agent according to the invention is intended for use in x-ray diagnosis, the central ion has to be derived from an element of a higher atomic number to achieve a sufficient absorption of the x rays. It has been found that, for this purpose, diagnostic agents which contain a physiologically compatible complex salt with central ions of elements of atomic numbers between 21–29, 39, 42, 44, 57–83 are suitable; these are, for example, the lanthanum(III) ion and the abovementioned ions of the lanthanide series.

For radiodiagnosis and radiotherapy, complexes are suitable which contain a radioisotope of elements 27, 29, 31, 32, 37–39, 43, 49, 62, 64, 70, 75 or 77 as a central ion. Here, a relatively small number of metal ions and thus the coupling of fewer macrocyclic complexing agents is necessary for the imaging.

Also, a complexing with different ions is desirable. Thus, for example, a polymeric gadolinium complex labeled partially with yttrium-90 can be used simultaneously for radiotherapy as well as for NMR-diagnostic control of the concentration.

In this way, it is possible to combine diagnosis and treatment with the help of the complex conjugates according to the invention.

As backbone molecules, to which macrocycle M is bound, all polymers are suitable which contain a plurality of amino, carboxy and/or hydroxy groups.

As examples, there can be mentioned polypeptides (such as, e.g., polylysine, polyornithine, polyarginine, polyasparaginic acid, polyglutamic acid, polyserine), polyallylamine, poly[N-(2-aminoethyl)]methacrylamides and polyamine carbohydrates (such as, e.g., polyaminodextran and chitosans). Polylysine is preferred; poly-L-lysine is especially preferred.

If the agent according to the invention is intended for use in NMR and x-ray diagnosis, n stands for the numbers 10 to 400, preferably for the numbers 10–200. If the agent according to the invention is intended for use in radiodiagnosis and radiotherapy, n stands for numbers 1 to 10.

Bridge-type crosslinks D, E, G, K contained in macrocycle M, which can be the same or different, consist of 2 to 5 $CH_2$ groups, and compounds with o meaning numbers 2 and/or 3 are preferred. As preferred complexing agent radicals, those of 1,4,7,10-tetraazacyclododecane-1,4,7-triacetic acid, 1,4,7-triazacyclononane-1,4-diacetic acid, 1,4,8,11-tetraazatetradecane-1,4,8-triacetic acid, or 1,5,9-triazacyclododecane-1,5-diacetic acid can be mentioned.

As preferred substituents $R^1$, the hydrogen atom, the methyl, the ethyl and benzyl group can be mentioned. The alkylene group or alkyl group standing for Z or R contains 1–20 C atoms and can be branched, unbranched, cyclic, saturated or unsaturated. The alkylene group standing for Z can be interrupted by 1–3, preferably 1 imino, phenylene, phenylenoxy, phenylenimino, and/or 1–5, preferably 1–3 amide, hydrazide, carbonyl groups and/or 1–7, preferably 1–5 ester groups, oxygen, sulfur and/or nitrogen atom or atoms and/or can have 1–5, preferably 1–3 hydroxy, mercapto, oxo, thioxo, carboxy, ester and/or amino groups. As preferred radicals, there can be mentioned as examples:

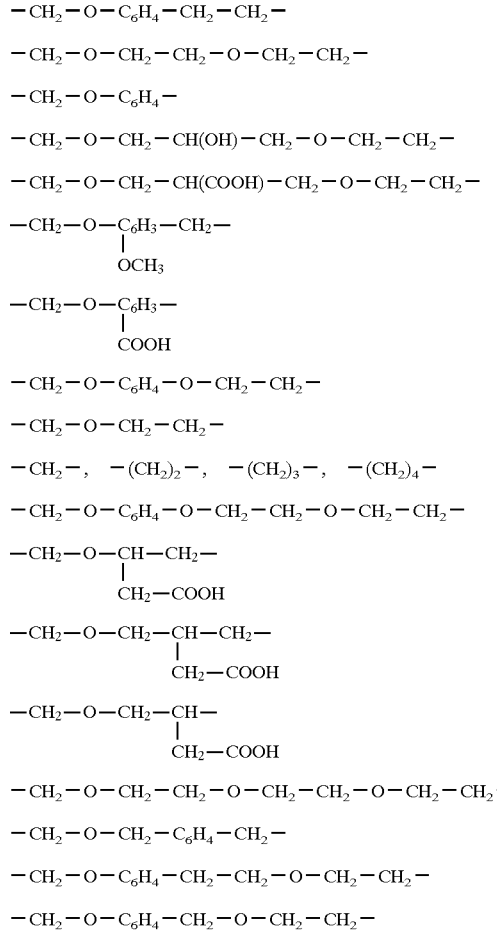

-continued

—C₆H₄—

—C₆H₄—O—CH₂—CH₂—

—C₆H₄—CH₂—

As radicals R, there can be mentioned as examples:

—CH₂COOH; —(CH₂)₂COOH; —CH(COOH)CH₂COOH; —CH₂—CH(COOH)CH₂OH;

—CH₂SO₃H; —(CH₂)₂SO₃H; —COCH₃; —COCH₂OH; —COCHOHCH₂OH; —COCH₂O—CH₂COOH;

—CO(CHOH)₄CH₂OH; —COCH₂COOH; —CO(CH₂)₂COOH; —CO(CH₂)₃COOH; —CO(CH₂)₄COOH;

—COCHOHCOOH; —CO(CHOH)₂COOH; —COCH₂CHOHCH₂COOH; —SO₂CH₂COOH; —SO₂(CH₂)₂COOH;

—SO₂CH₃;

—CO—CH₂—CH₂—CO—NH—CH₂—CONH—CH₂—COOH

—CO—CH₂—CH₂—CO—O—C₂H₅

—CO—CH₂—CH₂COO—CH₂—C₆H₅

—CO—CH₂—O—CH₂—CH₂—O—CH₂—CH₂—OCH₃

—CO—CH₂—C₆H₄—O—CH₂—CH₂—O—CH₂—CH₂—OCH₃

—CO—CH₂—CH₂—CONH—C₆H₄—O—CO—CH₃

—CO—CH₂—O—CO—C₇H₁₅

—CO—C₆H₄—O—CO—C₅H₁₁

—CO—CH₂—CH₂—(CH₂)₈—OH

—CO—CH₂—CH₂—CONH—CH(CH₃)—COOH

—COCH₂CH₂—COO—CH(CH₃)—CH₂—NHCO—CH₂OH

—CO—CH₂—CH₂—COO—CH—C₆H₄—O—CH₃
                              |
                             CH₃

—SO₂—CH₂—CH₂—CH₂—CH₂—CH₂—CH₃

—SO₂—C₆H₄—COOH

—CO—CH₂—O—CH₂—CH₂—O—CH₂—CH₂—OCH₃

—CO—CH₂—NH—CO—CH₂—O—CH₂—CH₂—OCH₃

—CO—C₆H₄—COO—Et

—CO—CH₂—CH₂—COO—CH₂—CH₂—OCO—CH₂—CH₂—CONH—CH₂—CONH—C₆H₅

The residual acidic hydrogen atoms existing in the polymer complex can optionally be substituted completely or partially by cations of inorganic and/or organic bases, amino acids or amino acid amides.

Suitable inorganic cations are, for example, the lithium ion, the potassium ion, the calcium ion, the magnesium ion and especially the sodium ion. Suitable cations of organic bases are, among others, those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acidic or neutral amino acids, such as, e.g., lysine methylamide, glycine ethylamide and serine methylamide.

The compounds according to the invention exhibit the initially described desired properties. They contain the large number of metal ions bound with stability to the complex necessary for their use. They are distributed only in the vascular space and can therefore label the latter with the help of nuclear spin tomography.

The value of the osmolality responsible for side effects such as pain, damage to the blood vessels and cardiovascular system disorders is clearly reduced.

The value for the relaxivity value representing a measurement of the imaging in MRI is surprisingly large; it was possible to increase the signal amplification e.g., in the case of the compound of example 4c relative to Magnevist®, by about 4 times.

In comparison with the macromolecular contrast media based on carbohydrates, e.g., dextran (European patent application, publication no. 0 326 226), which—as mentioned—generally have only 4.6% of the signal-amplifying paramagnetic cation, the polymer complexes according to the invention exhibit a content of over 15% of the paramagnetic cation. Thus, the macromolecules according to the invention per molecule bring about a very much greater signal amplification, whereby simultaneously the dose necessary for nuclear spin tomography is considerably smaller relative to the macromolecular contrast media on the basis of carbohydrates.

The complexes according to the invention can be used as contrast media to represent the vessels by nuclear spin tomography. It is thus possible to distinguish ischemic tissue from normal tissue. But also other damages to the bloodtissue barrier can be detected with these compounds. In inflammations and tumors in the brain, the blood-brain barrier is damaged so that the contrast medium can infiltrate the diseased tissue and thus the diseased tissue is detectable in nuclear spin tomography. Because of the impermeability of the intact blood-brain barrier also for small, but hydrophilic molecules, inflammations and tumors were also able to be detected already with the low-molecular weight compound Magnevist®. But if the complexes according to the invention are used in these cases, the dose can be reduced by 16 times for two reasons: 1. they have a signal amplification that is 4 times greater and 2. they are distributed in a space 4 times smaller, namely only in the vascular space, i.e., to reach the same concentrations in the blood, a quarter of the dose is sufficient.

Another advantage of this invention lies in the fact that now macrocyclic complexes of different molecular weight with hydrophilic or lipophilic properties have become accessible. As a result, the possibility is provided to control compatibility and pharmacokinetics of these polymer complexes by chemical substitution.

The production of the polymer compounds according to the invention takes place in that in a way known in the art, n molecules of general formula IA'

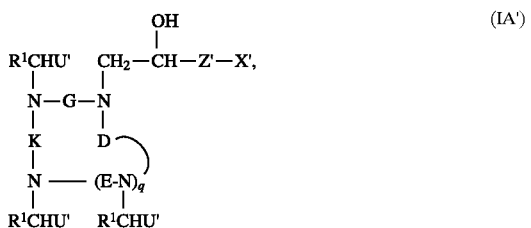

in which

Z' stands for Z or a direct bond,

U' stands for a $CO_2Y$ or $PO_3HY$ group with Y meaning a hydrogen atom, a metal ion equivalent of an element of atomic numbers 21–29, 31, 32, 37–39, 42–44 or 57–83 or an acid protecting group,

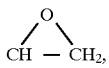

X' stands for a $C^*O$, $NH_2$, NCS, NCO, OFu, Hal, $COCH_2Hal$, CHO and anhydride group with $C^*O$ meaning an activated carbonyl group, Fu meaning a leaving group or a hydrogen atom and Hal meaning a fluorine, chlorine, bromine or iodine atom, are reacted with a backbone molecule A', which contains at least n amino, n hydroxy or n carboxy groups, then are optionally reduced and optionally are reacted with a reactant introducing substituent R, then optionally the acid protecting groups are removed and optionally reacted—in a way known in the art—with at least one metal oxide or metal salt of an element of atomic numbers 21–29, 31, 32, 37–39, 42–44 or 37–83 (and the metal complexing also can take place before the introduction of substituent R) and optionally then still present acidic hydrogen atoms are completely or partially substituted by cations of inorganic and/or organic bases, amino acids or amino acid amides.

As an example for an activated carbonyl group —$C^*O$— in compounds of general formula IA', anhydride, p-nitrophenylester, N-hydroxy-succinimide ester, acid chloride and a carboxylic acid activated in situ by a carbodiimide derivative can be mentioned, as an example for a leaving group, Cl, Br, I, $CH_3$—$C_6H_4$—$SO_3$, $CH_3SO_3$ and $CF_3SO_3$ can be mentioned.

As acid protecting groups, lower alkyl, aryl and aralkyl groups, for example, the methyl, ethyl, propyl, n-butyl, t-butyl, phenyl, benzyl, diphenylmethyl, triphenylmethyl, bis(p-nitrophenyl)-methyl group, as well as trialkylsilyl groups, are suitable.

The cleavage of the acid protecting groups takes place according to the processes known to one skilled in the art, for example, by hydrolysis, hydrogenolysis, alkaline saponification of esters with alkali in aqueous alcoholic solution at temperatures of 0° to 50° C., acid saponification with mineral acids or in the case of, e.g., tert-butyl esters with the help of trifluoroacetic acid.

The synthesis of the desired polymer compounds takes place by reaction of feedstocks of general formula IA', which contain leaving, activated carbonyl, amino, anhydride, isocyanate, isothiocyanate or aldehyde groups, with the amino or carboxy or hydroxy groups of the desired backbone molecules according to standard methods known in the literature, and in the case of the reaction of aldehyde groups with amino groups, a subsequent reduction has to be performed.

As selected examples for Z'–X' radicals, there can be mentioned:

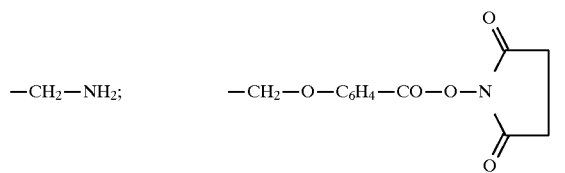

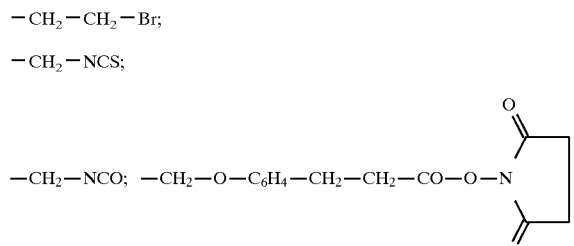

$-CH_2-O-(CH_2)_2-NCS$;

$-CH_2-O-(CH_2)_2-NH-CO-CH_2-Br$;

$-CH_2-O-SO_2-C_6H_4-CH_3$ $-CH_2-O-(CH_2)_2-O-(CH_2)_2-NCS$;

$-CH_2-O-CH_2-CHO$;

$-CHO$;

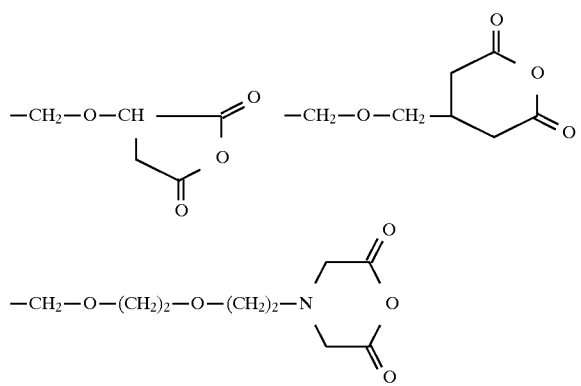

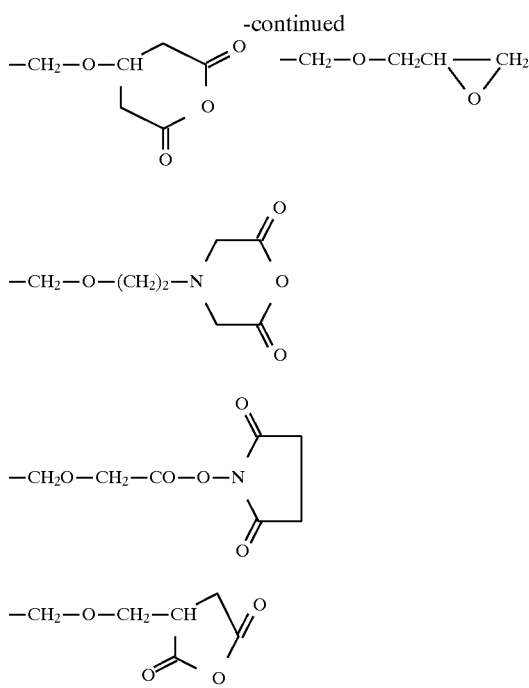

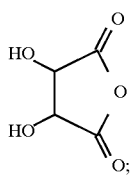

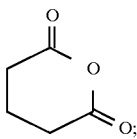

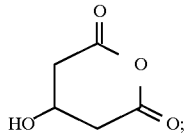

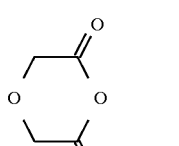

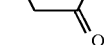

Br—CO—(CH$_2$)$_4$—COOC(CH$_3$)$_3$;  Cl—COCHOH—COOCH$_3$.

As an example for the reaction of an anhydride, the reaction of the gadolinium complex of 10-(6-[2,6-dioxomorpholino]-2-hydroxy-4-oxahexyl)-1,4,7-triscarboxymethyl-1,4,7,10-tetraazacyclododecane with the respectively desired backbone compounds containing primary amino groups in water or in mixtures of water with, e.g., dioxane, THF, DMF, DMSO or acetonitrile at basic pH, preferably 8–10, i.e., by adding bases such as, e.g., sodium hydroxide, potassium hydroxide or triethylamine, at temperatures of 0°–50° C., preferably at room temperature, can be mentioned. For complete reaction, the reaction is preferably performed with a, e.g., 2–3 times excess of anhydride.

Also, according to methods known in the literature, isothiocyanate-, epoxide- and α-haloacetyl-derivatized complexing agents or complexes are brought to reaction under pH control in aqueous medium with the desired amine-containing backbone compounds.

As another possibility, the reaction of macrocycles exhibiting terminal aldehyde groups with the respectively desired backbone compounds containing primary amino groups with subsequent reduction of the Schiff bases resulting in this way analogously to methods known in the literature (Synthesis 1975, 135) can be mentioned. The secondary amines generated in this case can be converted by subsequent acylation or alkylation with α,β-unsaturated esters, alkyl halides, anhydrides, acid halides or another macrocyclic compound IA' to tertiary amines, amides or thioamides. The reactants substituting secondary aminohydrogen atoms, mentioned as examples, can be listed:

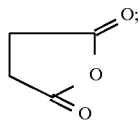

The aldehydes necessary as feedstocks in this case can be produced from the corresponding vicinal diols by oxidation with, for example, sodium metaperiodate in aqueous or alcoholic solution analogously to methods known in the literature (e.g., Makromol Chem. 182, 1641 [1981]).

By suitable performance of the reaction, e.g., adjustment of the pH or addition of amines, simultaneously introduced ester groups optionally can be saponified or aminolyzed.

The reaction of backbone (A') or macrocyclic (IA') compounds containing carboxy groups with macrocyclic (IA') or backbone (A') compounds containing amino and hydroxy groups also takes place according to standard methods (Houben-Weyl, Methoden der Organischen Chemie [Methods of Organic Chemistry], Georg-Thieme-Verlag, Stuttgart, Vol. XV/2 (1974), 1–364)

The purification of the thus obtained macrocyclic polymers takes place preferably by ultrafiltration with membranes of suitable pore size (e.g., Amicon® or gel filtration on, e.g., suitable Sephadex® gels.

The complexing agents of general formula IA' necessary as feedstocks can be produced, e.g., by reaction of, e.g., tri —CHR$^1$U' substituted tetraazacyclododecane derivatives known from European patent applications EP 255 471 and EP 287 465 with epoxides of general formula II

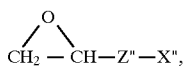  (II)

in which

Z" stands for radical Z', present in the optionally contained hydroxy, carboxy and amino groups in protected form and X" stands for a radical converted to X', in water or in water-miscible solvents, such as, e.g., acetonitrile, DMF, DMA, ethanol, methanol, dioxane, THF, DMSO, DME or their mixtures at temperatures of 0° C. to 170° C., preferably 20° to 100° C., within 12 to 48 hours, preferably 12 to 24 hours, by adding inorganic and/or organic bases, such as, e.g., potassium hydroxide, sodium hydroxide, lithium hydroxide, calcium hydroxide, barium hydroxide, magnesium hydroxide, sodium carbonate, potassium carbonate, triethylamine, tripropylamine, tributylamine, pyridine, DMPA, Reillex (), Triton B® and subsequent conversion of radical X" to X'.

As hydroxy protecting groups, all those are suitable which are easy to introduce and can also again be easily cleaved later by reformation of the finally desired free hydroxy group. Preferred protecting groups are ether groups, such as, for example, the benzyl, 4-methoxybenzyl, 4-nitrobenzyl, trityl, di- and triphenylmethyl, trimethylsilyl, dimethyl-t-butylsilyl, diphenyl-t-butylsilyl group. But the hydroxy groups in the form of ketals are preferably protected with, for example, acetone, acetaldehyde, cyclohexanone or benzaldehyde.

The cleavage of the hydroxy protecting groups takes place in a way known in the art, for example, in the case of a benzyl ether by reductive cleavage with lithium/ammonia or by hydrogenolytic cleavage in the presence of, for example, palladium-Carbon and in the case of an ether or ketal cleavage by acid treatment with the help of, for example, cation exchangers, trifluoroacetic acid or mineral acids [see, e.g., T. W. Greene "Protective Groups in organic.Synthesis," John Wiley and Sons (1981)].

As acid protecting groups, lower alkyl, aryl and aralkyl groups, for example, the methyl, ethyl, propyl, n-butyl, t-butyl, phenyl, benzyl, diphenylmethyl, triphenylmethyl, bis(p-nitrophenyl)-methyl group, as well as trialkylsilyl groups, are suitable.

The cleavage of the acid protecting groups takes place according to the processes known to one skilled in the art, for example, by hydrolysis, hydrogenolysis, alkaline saponification of the esters with alkali in aqueous alcoholic solution at temperatures of 0° to 50° C., acid saponification with mineral acids or in the case of, e.g., tert-butyl esters with the help of trifluoroacetic acid.

The amino groups are also protected, e.g., as tosylates, amides, trifluoroacetates, urethanes and benzylates and are later also released again according to processes known in the literature (cf., e.g., T. W. Greene "protective Groups in Organic Synthesis," John Wiley and Sons (1981)].

The functional groups $NH_2$, $NHCOCH_2Hal$, NCS and NCO desired as X' are generated after the alkylation with an epoxin of general formula II, in which X" stands for $—NO_2$ or $—N(CH_2–C_6H_5)_2$, according to methods known in the literature (European patent application publication no.: 292 689; U.S. Pat. No. 4,678,667; Bioconjugate Chem. 1990, 1, 59; J. Med. Chem., 1989, 32, 236).

The production of macrocycles IA', in which X' stands for C*O (e.g., mixed anhydride, N-hydroxy-succinimide ester, acylimidazoles, trimethylsilylester) takes place according to methods known in the literature [Houben-Weyl, Methoden der organischen Chemie, Georg Thieme Verlag, Stuttgart, Vol. E5 (1985), 633; Org. React. 12, 157 (1962)] or is described in the experimental part.

The epoxides II necessary as feedstocks are known or can be produced analogously to methods known in the literature, e.g., by reaction of alcohols with epichlorohydrin (Synthesis 1983, 117; Houben-Weyl, Methoden der organischen Chemie, Georg-Thieme-Verlag, Stuttgart, Vol. Vl/3 (1965), 369–487) and epoxidation of substituted allyl alcohols or unsaturated ethers (J. Org. Chem. 35, 215 (1970), Houben-Weyl, Georg-Thieme-Verlag Stuttgart 1965; Tetrahedron Lett. 1965, 849].

The thus obtained compounds of formula IA' are isolated after purification on silica gel columns, reversed-phase columns (RP-18) or on ion exchanger columns (e.g., IRA 67, IR 120, AMB 252).

The used backbone molecules A' can be produced according to methods known in the literature or also be purchased. Thus, polyallylamine can be obtained, e.g., from the Aldrich Chemical Company, polyaminodextrans and polypeptides, such as, e.g., polylysines of various molecular weights, polyasparaginic acid, polyglutamic acid, polyserine, etc., can be obtained from the Sigma Chemical Co. Polyaminodextrans can be produced according to U.S. Pat. No. 4,699, 784.

The production of the metal complexes according to the invention takes place in the way disclosed in German laid-open specification 34 01 052, by the metal oxide or a metal salt (for example, the nitrate, acetate, carbonate, chloride or sulfate of the element of atomic numbers 21–29, 31, 32, 37–39, 42–44, 47, 49, 57–83) being dissolved or suspended in water and/or a lower alcohol (such as methanol, ethanol or isopropanol) and reacted with the solution or suspension of the equivalent amount of the complexing ligands and then, if desired, present acidic hydrogen atoms being substituted by cations of inorganic and/or organic bases or amino acids.

The introduction of the desired metal ions in this case can take place both before and after the reaction of macrocycle I' with A'. In the case of the radioactively-labeled polymer complexes, the introduction of the radioisotopes is preferably performed in the last reaction stage. If a complexing with different ions is desired. Thus, for example, in the treatment of tumors with yttrium-90, first a number of gadolinium ions necessary for nuclear spin tomography can be introduced and later on metal atoms of complexing agents that remain uncomplexed or vacant, present on the finished conjugate, can be labeled with the radioisotope (see examples 13 and 14). In this way, it is possible to combine diagnosis and treatment with the help of the complex conjugates according to the invention.

The neutralization of possibly still present free carboxy groups takes place with the help of inorganic bases (e.g., hydroxides, carbonates or bicarbonates) of, e.g., sodium, potassium, lithium, magnesium or calcium and/or organic bases, such as, among others, primary, secondary and tertiary amines, such as, e.g., ethanolamine, morpholine, glucamine, N-methyl and N,N-dimethylglucamine, as well as basic amino acids, such as, e.g., lysine, arginine and ornithine or of amides of originally neutral or acid amino acids.

For the production of neutral complex compounds, for example, so many of the desired bases can be added to the acid complex salts in aqueous solution or suspension that the neutral point is reached. The obtained solution can then be evaporated to dryness in a vacuum. Often, it is advantageous to precipitate the formed neutral salts by adding water-miscible solvents, such as, e.g., lower alcohols (methanol, ethanol, isopropanol and others), lower ketones (acetone and others), polar ethers (tetrahydrofuran, dioxane, 1,2-dimethoxyethane and others) and thus to obtain crystallizates that are easy to isolate and easy to purify. It has proven especially advantageous to add the desired base already during the complexing of the reaction mixture and as a result to dispense with a process step.

The production of the pharmaceutical agents according to the invention also takes place in a way known in the art, by the complex compounds according to the invention— optionally by adding the additives usual in galenicals— being suspended or dissolved in aqueous medium and then the suspension or solution optionally being sterilized. Suitable additives are, for example, physiologically harmless buffers (such as, for example, tromethamine), additives of complexing agents (such as, for example, diethylenetriaminepentaacetic acid) or—if necessary—electrolytes, such as, for example, sodium chloride or—if necessary—antioxidants, such as, for example, ascorbic acid.

If suspensions or solutions of the agents according to the invention in water or physiological salt solution are desired for enteral administration or other purposes, they are mixed with one or more auxiliary agent or agents usual in galenicals (for example, methyl cellulose, lactose, mannitol) and/or surfactant or surfactants (for example, lecithins, Tween®, Myrj®) and/or aromatic substance or substances for taste correction (for example, essential oils).

In principle, it is also possible to produce the pharmaceutical agents according to the invention also without isolating the complex salts. In each case, special care then has to be used to carry out the chelate formation, so that the salts and salt solutions according to the invention are practically free of noncomplexed, toxic-acting metal ions.

This can be assured, for example, with the help of color indicators, such as xylenol orange by control titrations during the production process. The invention therefore relates also to the process for the production of complex compounds and their salts. As a final safety, there remains a purification of the isolated complex salt.

The pharmaceutical agents according to the invention contain preferably 0.1 $\mu$mol–3 mol/l of the complex salt and are generally dispensed in amounts of 0.1 $\mu$mol–5 mmol/kg. They are intended for enteral and parental administration. The complex compounds according to the invention are used:

1. for NMR and x-ray diagnosis in the form of their complexes with the ions of the elements with atomic numbers 21–29, 42, 44 and 57–83;
2. for radiodiagnosis and radiotherapy in the form of their complexes with the radioisotopes of the elements with atomic numbers 21, 26, 27, 29, 31, 32, 37–39, 43, 47, 49, 62–64, 67, 70, 71, 75, 77, 79 and 83.

The agents according to the invention meet the varied requirements for suitability as contrast media for nuclear spin tomography. Thus, they are excellently suited, after enteral or parenteral administration by increasing the signal intensity, to improve the image, obtained with the help of nuclear spin tomography, in its informative value. Further, they show the high effectiveness, which is necessary to load the body with the smallest possible amounts of foreign substances, and the good compatibility, which is necessary to maintain the noninvasive nature of the tests.

The good water solubility and low osmolality of the agents according to the invention make it possible to produce highly concentrated solutions, thus to keep the volume load of the circulatory system to justifiable limits and to compensate for the dilution by the body fluid, i.e., NMR diagnostic agents have to be 100 to 1000 times more water-soluble than for NMR spectroscopy. Further, the agents according to the invention exhibit not only a high stability in vitro, but also a surprisingly high stability in vivo, so that a release or an exchange of the ions—toxic in themselves—not covalently bound in the complexes, takes place only extremely slowly within the time in which the new contrast media are again completely eliminated.

In general, the agents according to the invention for use as NMR diagnostic agents are dispensed in amounts of 0.0001–5 mmol/kg, preferably 0.005–0.5 mmol/kg. Details of the use are discussed, for example, in H. J. Weinmann et al., Am. J. of Roentgenology [Am. J. of Radiology] 142, 619 (1984).

Further, the complex compounds according to the invention advantageously can be used as susceptibility reagents and as shift reagents for in vivo NMR spectroscopy.

The agents according to the invention are also suitable as radiodiagnostic agents because of their advantageous radioactive properties and the good stability of the complex compounds contained in them. Details of their use and dosage are described, e.g., in "Radiotracers for Medical Applications," CRC Press, Boca Raton, Fla.

Another imaging method with radioisotopes is positron emission tomography, which uses positron-emitting isotopes, such as, e.g., $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, N.Y. 1983).

The compounds according to the invention can also be used in radioimmunotherapy or radiation therapy. The latter is distinguished from the corresponding diagnosis only by the amount and type of isotope used. The purpose in this case is the destruction of tumor cells by high-energy short-wave radiation with a lowest possible range of action. Suitable $\beta$-emitting ions are, for example, $^{46}$Sc, $^{47}$Sc, $^{48}$Sc, $^{72}$Ga, $^{73}$Ga and $^{90}$Y. Suitable $\alpha$-emitting ions exhibiting short half-lives are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variants of radiation therapy proposed by R. L. Mills et al. [Nature Vol. 336, (1988), p. 787], the central ion has to be derived from a Moessbauer isotope, such as, for example, $^{57}$Fe or $^{151}$Eu.

In the in vivo administration of the therapeutic agents according to the invention, the latter can be administered together with a suitable vehicle, such as, for example, serum or physiological common salt solution and together with another protein, such as, for example, human serum albumin. The dosage is dependent in this case on the type of cellular disorder, the metal ion used and the type of method, e.g., brachytherapy.

The therapeutic agents according to the invention are administered parenterally.

Details of use of radiotherapeutic agents are discussed, e.g., in R. W. Kozak et al. TIBTEC, October 1986, 262.

The agents according to the invention are excellently suited as x-ray contrast media, and it is especially to be emphasized that with them, no signs of the anaphylactic-type reactions in biochemical-pharmacological tests known from the contrast media containing iodine can be detected. They are especially valuable because of the advantageous absorption properties in the areas of higher tube voltages for digital subtraction techniques.

To use a wide range of x-ray radiation, it is often advantageous to have two or more than two different metals bound to the polymer complex.

In general, the agents according to the invention are dispensed for use as x-ray contrast media analogously to, for example, meglumine-diatrizoate in amounts of 0.1–5 mmol/kg, preferably 0.25–1 mmol/kg.

Details of use of x-ray contrast media are discussed, for example, in Barke, Röntgenkontrastmittel [X-ray Contrast Media], G. Thieme, Leipzig (1970) and P. Thurn, E. B ücheler— "Einführung in die Röntgendiagnostik" [Introduction to X-ray Diagnosis], G. Thieme, Stuttgart, New York. (1977).

Another advantage of the macrocyclic polymer complexes according to the invention lies in the nuclear medical use for diagnosis and/or treatment of malignant tumors by bispecific antibodies (K. G. Burnett et al., Biotechnology; Appl. Res. 1983, 31, 401). These bispecific (bifunctional) antibodies are directed against two different antigens, e.g., against a tumor antigen and against the polymer complexes according to the invention. As a result, the antibody can be located on or in the tumor before the administration of the radioactively labeled complex. Then, the radioactively labeled polymer intended for diagnosis or for treatment is administered, which is immobilized at the desired point by the second specificity of the antibody. Recently, i.a., the production of humanized mouse-IgG's by genetic engineering was described (J. L. Phelps et al., J. Immunol. 1990, 145, 1200), which are especially suitable for use with humans. Also, bispecific antibodies for nuclear resonance and x-ray diagnosis can be obtained in this way.

Altogether, it has been possible to synthesize new complexing agents, metal complexes and metal complex salts, which open up new possibilities in diagnostic and therapeutic medicine. Above all, the development of new type imaging processes in medical diagnosis makes this development appear to be desirable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 15 789.3, filed May 10, 1991, are hereby incorporated by reference.

EXAMPLES

Example 1 a) 1,2-Epoxy-3-dibenzylaminopropane 100 g (506.9 mmol) of dibenzylamine (dissolved in 300 ml of dichloromethane) is instilled in a well-stirred suspension of 234.51 g (2.53 mol) of epichlorohydrin and 200 ml of 32% sodium hydroxide solution at 0° C. It is stirred for 2 hours at 0° C., then for 3 hours at room temperature. It is diluted with 3 l of water and extracted 3 times with 500 ml of dichloromethane. The organic phases are combined, dried on magnesium sulfate and concentrated by evaporation in a vacuum. The remaining oil is "flash"-Chromatographed on silica gel (mobile solvent: dichloromethane/hexane/acetone: 20/10/3).

Yield: 111.72 g (87% of theory) of a colorless oil; Analysis (relative to anhydrous substance): C 80.60 H 7.56 N 5.53 Cld., C 80.62 H 7.50 N 5.48 b) 10-(3-Dibenzylamino-2-hydroxypropyl)-1,4,7:-triscarboxymethyl-1,4,7,10-tetraazacyclododecane 20 g (78.95 mmol) of the title compound of example 1a and 20.51 g (59.21 mmol) of 1,4,7-triscarboxymethyl-1,4,7,10-tetraazacyclododecane (DO3A) are dissolved in a mixture of 50 ml of dioxane and 200 ml of water, and the pH is brought to pH 10 with 6N potassium hydroxide solution. It is stirred for 24 hours at 40° C. It is evaporated to dryness, the residue is taken up with 500 ml of water/500 ml of methanol and extracted twice with 200 ml of tert-butyl-methyl ether. The aqueous solution is adjusted to pH 3 with 5N hydrochloric acid and evaporated to dryness. The residue is concentrated by evaporation in a vacuum and then poured on a column of poly-(4-vinylpyridine). The product is eluted with a solution of ethanol/water 1:1. After concentration by evaporation in a vacuum, 22.37 g (63% of theory) of a strongly hygroscopic, vitreous solid (6.9% water according to analysis) is obtained.

Analysis (relative to anhydrous substance): C 62.08 H 7.56 N 11.68 Cld. C 62.15 H 7.61 N 11.61 c) Gadoliniumcomplexof 10-(3-dibenzylamino-2-hydroxypropyl)-1,4,7-tris-carboxymethyl-1,4,7,10-tetraazacyclododecane 21 g (35.02 mmol) of the title compound of example 1b is dissolved in a solution of 150 ml of deionized water/50 ml of methanol and 6.35 g (17.51 mmol) of gadolinium oxide is added. It is refluxed for 2 hours. 3 g of activated carbon is added. The solution is hot-filtered and the filtrate is evaporated to dryness in a vacuum.

Yield: 25.08 g (95% of theory) of a vitreous solid (5.2% water according to analysis); Analysis (relative to anhydrous substance): C 49.39 H 5.61 N 9.29 Gd 20.86 Cld., C 49.41 H 5.70 N 9.25 Gd 20.88 d) Gadolinium complex of 10-(3-amino-2-hydroxypropyl)-1,4,7-triscarboxymethyl-1,4,7,10-tetraazacyclododecane 24 g (31.83 mmol) of the title compound of example 1c is dissolved in a mixture of 250 ml of deionized water/150 ml of methanol and 2 g of Pearlman's catalyst (20% palladium hydroxide on activated carbon) is added. Then, it is hydrogenated for 24 hours at 50° C. It is filtered off from the catalyst and the filtrate is concentrated by evaporation in a vacuum.

Yield: 17.89 g (98% of theory) of a vitreous solid (6.4% water according to analysis)

Analysis (relative to anhydrous substance): C 35.59 H 5.27 N 12.21 Gd 27.41 Cld. C 35.51 H 5.34 N 12.16 Gd 27.36 e) Gadolinium complex of 10-(3-isothiocyanato-2-hydroxypropyl)-1,4,7-triscarboxymethyl-1,4,7-10-tetraazacyclododecane A solution of 4.81 g (41.83 mmol) of thiophosgene in 100 ml of chloroform is added to a solution of 12 g (20.92 mmol) of the title compound of example 1d in 500 ml of deionized water and 20 ml of polyvinylpyridine (Reillex). The two-phase solution is stirred for 10 minutes at 40° C., then for one hour at room temperature and filtered. The organic phase is separated and the water phase is subsequently extracted twice with 200 ml of chloroform. Then, the water phase is freeze-dried.

Yield: 12.62 g (98% of theory) of a colorless powder (5.7% water according to analysis); Analysis (relative to anhydrous substance): C 35.11 H 4.58 N 11.37 S 5.21 Gd 25.54 Cld. C 35.04 H 4.64 N 11.31 S 5.15 Gd 25.48 f) Thioureido conjugate of the Gd complex of 10-(3-isothiocyanato-2-hydroxypropyl)-1,4,7-triscarboxymethyl-1,4,7,10-tetraazacyclododecane with poly-L-lysine 2.09 g of poly-L-lysine-hydrobromido [Sigma], 10 mmol, is dissolved in 25 ml of $H_2O$ and released to amine rapidly by an anion exchange column (10 ml of Amberlite® IRA 410, OH form). 7.39 g (12 mmol) of the isothiocyanate-Gd complex described in example 1e is added in solid form to this basic solution under nitrogen and stirred overnight at room temperature. After ultrafiltration (Amicon® YM-5-membrane), the conductivity of the solution is adjusted to a minimum by ion exchanger (Amberlite® IR 120, $H^+$ form, and IRA 410, OH form). It is filtered off from the exchanger and freeze-dried.

Yield: 7.12 g (89% of theory) $H_2O$ content (Karl-Fischer): 7.03% Gd determination (AAS): 18.72% $T_1$ relaxivity (H2O): 11.83±0.42 [l/mmol.sec] $T_1$ relaxivity (plasma):

11.99±0.57 [l/mmol.sec] Analysis (relative to anhydrous substance): C 38.75 H 5.42 Gd 21.14 N 13.18 S 4.31 Cld. C 39.11 H 5.57 Gd 19.83 N 12.87 S 4.01

Example 2 a) 1-Dibenzylamino-5,6-epoxy-3-oxahexane 100 g (414 mmol) of N-dibenzylaminoethanol is dissolved in 200 ml of dichloromethane and instilled at 0° C. in a vigorously stirred mixture of 250 ml of 50% sodium hydroxide solution, 7.03 g (20.7 mmol) of tetra-n-butylammonium hydrogen sulfate and 153.4 g (1.657 mol) of epichlorohydrin. It is stirred for 8 hours at 0° C. overnight at room temperature. It is diluted with 2 l of water and extracted 3 times with 500 ml of dichloromethane. The combined organic phases are dried on magnesium sulfate and concentrated by evaporation in a vacuum. The remaining oil is subjected to a flash chromatography on silica gel. (Mobile solvent: dichloromethane/hexane/acetone 20/10/3).

Yield: 96.12 g (78% of theory) of a colorless oil; Analysis (relative to anhydrous substance): C 76.74 H 7.79 N 4.71 Cld. C 76.68 H 7.85 N 4.66 b) 10-(6-Dibenzylamino-2-hydroxy-4-oxahexyl)-1,4,7-triscarboxymethyl-1,4,7,10-tetraazacyclododecane 34.34 g (115.47 mmol) of the title compound of example 2a and 20 g (57.74 mmol) of 1,4,7-triscarboxymethyl-1,4,7,10-tetraazacyclododecane (DO3A) are dissolved in a mixture of 60 ml of dioxane/350 ml of water and the pH is adjusted to pH 10 with 6N potassium hydroxide solution. It is stirred for 24 hours at 40° C. It is worked up as described under example 1b.

Yield: 26.39 g (71% of theory) of a vitreous solid (7.1% water according to analysis); Analysis (relative to anhydrous substance): C 61.57 H 7.67 N 10.88 Cld. C 61.49 H 7.80 N 10.79 c) Gadolinium complex of 10-(6-dibenzylamino-2-hydroxy-4-oxahexyl)-1,4,7-triscarboxymethyl-1,4,7,10-tetraazacyclododecane 23 g (35.73 mmol) of the title compound of example 2b is dissolved in a solution of 150 ml of deionized water/50 ml of methanol and 6.48 g (17.86 mmol) of gadolinium oxide is added. It is refluxed for 2 hours. 3 g of activated carbon is added and it is refluxed for a second hour. The solution is hot-filtered and the filtrate is evaporated to dryness in a vacuum.

Yield: 27.65 g (97% of theory) of a vitreous solid (7.8% water according to analysis); Analysis (relative to anhydrous substance): C 49.67 H 5.81 N 8.78 Gd 19.71 Cld. C 49.61 H 5.89 N 8.71 Gd 19.61 d) Gadolinium complex of 10-(6-amino-2-hydroxy-4-oxahexyl)-1,4,7-triscarboxymethyl-1,4,7,10-tetraazacyclododecane 25 g (31.33 mmol) of the title compound of example 2c is dissolved in a mixture of 250 ml of deionized water/150 ml of methanol and 2 g of Pearlman's catalyst (20% palladium hydroxide on activated carbon) is added. Then, it is hydrogenated for 24 hours at 50° C. It is filtered off from the catalyst and the filtrate is concentrated by evaporation in a vacuum.

Yield: 19.16 g (99% of theory) of a vitreous solid (5.7% according to analysis); Analysis (relative to anhydrous substance): C 36.94 H 5.55 N 11.34 Gd 25.45 Cld. C 36.88 H 5.59 N 11.27 Gd 25.38 e) Gadolinium complex of 10-(6-isothiocyanato-2-hydroxy-4-oxahexyl)-1,4,7-triscarboxymethyl-1,4,7,10-tetraazacyclododecane A solution of 5.58 g (48.56 mmol) of thiophosgene in 100 ml of chloroform is added to a solution of 15 g (24.28 mmol) of the title compound of example 2d in 500 ml of deionized water and 20 ml of polyvinylpyridine (Reillex). The two-phase solution is stirred for 10 minutes at 40° C., then for one hour at room temperature and filtered. The organic phase is separated and the water phase is extracted twice with 200 ml of chloroform. Then, the water phase is freeze-dried.

Yield: 15.7 g (98% of theory) of a colorless powder (6.1% water according to analysis); Analysis (relative to anhydrous substance): C 36.41 H 4.89 N 10.61 Gd 23.83 S 4.86 Cld. C 36.35 H 4.95 N 10.51 Gd 23.71 S 4.78 f) Thioureido conjugate of the Gd complex of 10-(6-isothiocyanato-2-hydroxy-4-oxahexyl)-1,4,7-triscarboxymethyl-1,4,7,10-tetraazacyclododecane with poly-L-lysine 2.09 g of poly-L-lysine-hydrobromide [Sigma], 10 mmol, is dissolved in 25 ml of $H_2O$ and released to the amine rapidly by an anion exchange column (10 ml of Amberlite® IRA 410, OH form). 7.92 g (12 mmol) of the isothiocyanate-Gd complex described in example 2e is added to this basic solution under nitrogen and the suspension is stirred overnight at room temperature. After ultrafiltration (Amicon® YM-5-membrane), the conductivity of the solution is adjusted to a minimum by ion exchanger (Amberlite® IR 120, $H^+$ form, and IRA 410, OH form). It is filtered off from the exchanger and freeze-dried.

Yield: 7.49 g (91% of theory) $H_2O$ content (Karl-Fischer): 4.26% Gd determination (AAS): 18.39% $T_1$-relaxivity ($H_2O$): 12.34±0.12 [l/mmol.sec] $T_1$-relaxivity (plasma): 12.13±0.47 [l/mmol.sec]; Analysis (relative to anhydrous substance): C 39.63 H 5.63 Gd 19.96 N 12.44 S 4.07 Cld. C 40.13 H 5.84 Gd 19.07 N 12.15 S 3.84

Example 3 a) 1-Dibenzylamino-5-hydroxy-3-oxapentane

A mixture of 50 g (475.56 mmol) of 2-(2-amino-ethoxy)-ethanol and 144.6 g (1.046 mol) of potassium carbonate in 600 ml of ethanol/60 ml of water is heated to 60° C. 178.95 g (1.046 mol) of benzyl bromide is instilled in this mixture within 1 hour and then refluxed for 2 hours. It is concentrated by evaporation in a vacuum, the residue is taken up with 1 l of dichloromethane and filtered off from the salts. The filtrate is concentrated by evaporation in a vacuum and purified by flash chromatography on silica gel. (Mobile solvent: dichloromethane/hexane/acetone: 10/5/1)

Yield: 127.58 g (94% of theory) of a colorless oil; Analysis (relative to anhydrous substance): C 75.76 H 8.12 N 4.91 Cld. C 75.71 H 8.18 N 4.85 b) 1-Dibenzylamino-8,9-epoxy-3,6-dioxanonane

A solution of 125 g (438 mmol) of the title compound of example 3a in 200 ml of dichloromethane is instilled in a well-stirred suspension of 162.11 g (1.752 mol) of epichlorohydrin, 8.2 g (24.15 mmol) of tetra-n-butylammonium hydrogen sulfate and 250 ml of 50% sodium hydroxide solution at 0° C. It is stirred for 8 hours at 0° C., overnight at room temperature. It is diluted with 2 l of water and extracted twice with 500 ml of dichloromethane. The combined organic phases are dried on magnesium sulfate and concentrated by evaporation in a vacuum. The remaining oil is purified by flash chromatography on silica gel (mobile solvent: dichloromethane/hexane/acetone: 20/10/3).

Yield: 116.5 g (78% of theory) of a colorless oil; Analysis (relative to anhydrous substance): C 73.87 H 7.79 N 4.10 Cld. C 73.78 H 7.95 N 4.03 c) 10-(9-Dibenzylamino-2-hydroxy-4,7-dioxanonyl)-1,4,7-triscarboxymethyl-1,4,7,10-tetraazacyclododecane 39.43 g (115.47 mmol) of the title compound of example 3b and 20 g (57.74 mmol) of 1,4,7-triscarboxymethyl-1,4,7,10-tetraazacyclododecane (DO3A) are dissolved in a mixture of 60 ml of dioxane/250 ml of water and the pH is adjusted to pH 10 with 6N potassium hydroxide solution. It is stirred for 24 hours at 40° C. Then, it is worked up as described in example 1b.

Yield: 28.59 g (72% of theory) of a vitreous solid (6.3% water according to analysis); Analysis (relative to anhydrous substance): C 61.12 H 7.77 N 10.18 Cld. C 61.07 H 7.84 N 10.05 d) Gadolinium complex of 10-(9-dibenzylamino-2-hydroxy-4,7-dioxanonyl)-1,4,7-triscarboxymethyl-1,4,7,10-tetraazacyclododecane 25 g (36.35 mmol) of the title compound of example 3c is dissolved in a solution of 150 ml of deionized water/50 ml of methanol and 6.59 g (18.17 mmol) of gadolinium oxide is added. It is refluxed for 2 hours. 3 g of activated carbon is added and refluxed for a second hour. The solution is hot-filtered and the filtrate is evaporated to dryness in a vacuum.

Yield: 30.0 g (98% of theory) of a vitreous solid (5.4% water according to analysis); Analysis (relative to anhydrous substance): C 49.92 H 5.98 N 8.32 Gd 18.67 Cld. C 49.83 H 5.90 N 8.34 Gd 18.58

In an analogous way, the corresponding europium complex is obtained with $^{151}Eu_2O_3$. Analysis (relative to anhydrous substance): C 50.24 H 6.02 N 8.37 Eu 18.16 Cld. C 50.17 H 5.96 N 8.26 Eu 18.09 e) Gadolinium complex of l0-(9-amino-2-hydroxy-4,7-dioxanonyl)-1,4,7-triscarboxymethyl-1,4,7,10-tetraazacyclododecane 29 g (34.44 mmol) of the title compound of example 3d is added to a mixture of 250 ml of deionized water/150 ml of methanol and 2 g of Pearlman's catalyst (20% palladium hydroxide on activated carbon). Then, it is hydrogenated for 24 hours at 50° C. It is filtered off from the catalyst and the filtrate is concentrated by evaporation in a vacuum.

Yield: 22.56 g (99% of theory) of a vitreous solid (6.5% water according to analysis); Analysis (relative to anhydrous substance): C 38.11 H 5.79 N 10.58 Gd 23.76 Cld. C 38.05 H 5.86 N 10.47 Gd 23.65 f) Gadolinium complex of 10-(9-isothiocyanato-2-hydroxy-4,7-dioxanonyl)-1,4,7-triscarboxymethyl-1,4,7,10-tetraazacyclododecane A solution of 5.21 g (45.33 mmol) of thiophosgene in 100 ml of chloroform is added to a solution of 15 g (22.66 mmol) of the title compound of example 3e in 500 ml of deionized water and 20 ml of polyvinylpyridine (Reillex). The two-phase solution is stirred for 10 minutes at 40° C., then for one hour at room temperature and filtered. The organic phase is separated and the water phase is extracted twice with 200 ml of chloroform. Then, the water phase is freeze-dried.

Yield: 15.64 g (98% of theory) of a colorless powder (5.9% water according to analysis); Analysis (relative to anhydrous substance): C 37.54 H 5.15 N 9.95 Gd 22.34 S 4.55 Cld. C 37.49 H 5.11 N 9.91 Gd 22.27 S 4.61 g) Thioureido conjugate of the Gd complex of 10-(9-isothiocyanato-2-hydroxy-4,7-dioxanonyl)-1,4,7-triscarboxymethyl-1,4,7,10-tetraazacyclododecane with poly-L-lysine 2.09 g of poly-L-lysine-hydrobromide [Sigma], 10 mmol, is dissolved in 25 ml of $H_2O$ and released to amine rapidly by an anion exchange column (10 ml of Amberlite® IRA 410, OH form). 8.45 g (12 mmol) of the isothiocyanate-Gd complex described in example 3f is added in solid form to this solution under nitrogen and stirred overnight at room temperature. After ultrafiltration (Amicon® YM-5-membrane), the conductivity of the solution is adjusted to a minimum by ion exchanger (Amberlite® IR 120, $H^+$ form, and IRA 410, OH form). It is filtered off from the exchanger and freeze-dried.

Yield: 7.24 g (81.4% of theory) $H_2O$ content (Karl-Fischer): 6.50% Gd determination (AAS): 15.89% $T_1$ relaxivity ($H_2O$): 11.75±0.37 [l/mmol.sec] $T_1$ relaxivity (plasma): 13.07±0.14 [l/mmol.sec]; Analysis (relative to anhydrous substance): C 40.42 H 5.81 Gd 18.90 N 11.78 S 3.85 Cld. C 40.33 H 5.99 Gd 17.23 N 11.95 S 3.47

Example 4 a) 10-[2,6,7-Trihydroxy-4-oxa-heptyl]-1,4,7-triscarboxymethyl-1,4,7,10-tetraazacyclododecane 19.56 g (103.92 mmol) of 2,2-dimethyl-4-(2',3'-epoxy)-propoxy-methyl-1,3-dioxolane.and 10 g (28.86 mmol) of 1,4,7-triscarboxymethyl-1,4,7,10-tetraazacyclododecane (DO3A) are dissolved in a mixture of 50 ml of dioxane/80 ml of water and the pH is brought to pH 10 with 6N potassium hydroxide solution. It is stirred for 24 hours at 70° C. It is evaporated to dryness, the residue is taken up with 200 ml of water/50 ml of methanol and extracted twice with 100 ml of tert-butyl-methyl ether. The aqueous solution is adjusted to pH 3 with 5N hydrochloric acid and evaporated to dryness. The residue is boiled out (extracted) with 200 ml of methanol/80 ml of dichloromethane. It is cooled in an ice bath and filtered off from the precipitated potassium chloride. The filtrate is concentrated by evaporation in a vacuum, the residue is dissolved in 45 ml of water/20 ml of ethanol and then poured on a column of poly-(4-vinylpyridine). The product is eluted with a solution of ethanol/water 1:3. After concentration by evaporation in a vacuum, the residue is chromatographed on a reversed phase column (RP 18/mobile solvent=gradient of water/tetrahydrofuran). After concentration by evaporation of the main fraction, 10.13 g (71% of theory) of a strongly hygroscopic, vitreous solid is obtained. Analysis (relative to anhydrous substance): C 48.57 H 7.74 N 11.33 Cld. C 48.46 H 7.81 N 11.24 b) Gd Complex of 10-(2,6,7-trihydroxy-4-oxa-heptyl)-1,4,7-tris-carboxymethyl-1,4,7,10-tetraazacyclododecane 8.56 g (17.3 mmol) of the title compound of example 4a is dissolved in 50 ml of deionized water and 3.13 g (8.65 mmol) of gadolinium oxide is added. It is heated for 3 hours to 90° C. The cooled solution is stirred for one hour with 3 ml of acid ion exchanger (AMB 252 c) and 3 ml of weakly basic exchanger (IRA 67). It is filtered off from the exchanger and the filtrate is freeze-dried.

Yield: 11.0 g (98% of theory) of a colorless, amorphous powder; Analysis (relative to anhydrous substance): C 37.03 H 5.44 N 8.64 Gd 24.24 Cld. C 37.00 H 5.51 N 8.57 Gd 24.18 c) Gd Complex of $N^5$-{6-[4,7,10-tris-(carboxymethyl)-1,4,7,10-tetraazacyclododecan-1-yl]-5-hydroxy-3-oxa-hexyl}-poly-L-lysine 38.93 g (60 mmol) of the Gd complex of example 4b is dissolved in 400 ml of methanol, mixed with 12.83 g (60 mmol) of $NaIO_4$ and stirred for 2 hours with exclusion of light. Then, it is filtered off from insolubles and the filtrate is freeze-dried. The lyophilizate is dissolved in as little water as possible and reprecipitated with ethanol/ether (3:1). The precipitate is suctioned off, dissolved with 4.94 g (30 mmol) of poly-L-lysine-hydrochloride in 750 ml of buffer of pH 9.0 (Riedel de Haën, Borax/HCl) and stirred with exclusion of light after adding 7.55 g (120 mmol) of sodium cyanoborohydride for 6 days at room temperature. The solution is then ultrafiltered (Amicon YM-5-membrane) and then freeze-dried.

Yield: 15.0 g (61.0% of theory) $H_2O$ content (Karl-Fischer): 11.1% Gd determination (AAS): 15.76% $T_1$ relaxivity ($H_2O$): 18.30±0.14 [l/mmol.sec] $T_1$ relaxivity (plasma): 18.20±0.33 [l/mmol.sec]

Example 5

Gd Complex of $N^5$-{6-[4,7,10-tris-(carboxymethyl)-1,4,7,10-tetraazacyclododecan-1-yl]-5-hydroxy-3-oxa-hexyl}-$N^5$-(2-carboxyethyl)-poly-L-lysine 2.20 g of the polymer described in example 4c with secondary amine in the linkages between complex and polylysine is suspended in 25 ml of methanol/$H_2O$ (5:1) and a mixture of 20 ml (220 mmol) of methyl acrylate and 20 ml of methanol is added and stirred for 3 days at room temperature. The solution is concentrated by evaporation in a vacuum, the residue is dissolved in 20 ml of 1N NaOH and saponified for 3 hours at room temperature. Then, it is neutralized with dilute HCl and the solution is desalted by an Amicon ultra-filtration membrane YM5 and finally freeze-dried.

Yield: 2.20 g $H_2O$ content (Karl-Fischer): 5.76% Gd determination (AAS): 15.42% $T_1$ relaxivity ($H_2O$): 12.39±0.37 [l/mmol.sec] $T_1$ relaxivity (plasma): 12.87±0.09 [l/mmol.sec]

The paper electrophoresis of the polymer at pH 9.0 (0.05 M borax) and 10 V/cm shows a migration to the anode, while the initial compound (example 4c) migrates to the cathode under the same conditions.

Example 6

Gd Complex of $N^5$-{6-[4,7,10-tris-(carboxymethyl)-1,4,7,10-tetraazacyclododecan-1-yl]-5-hydroxy-3-oxa-hexyl}-$N^5$-(2-dicarboxyethyl)-poly-L-lysine 23 ml of triethylamine is instilled in 14.3 g (110 mmol) of maleic acid-monomethyl ester (Tokyo Chemical Co. Ltd.) in 15 ml of methanol under ice cooling. It is allowed to heat to room temperature and this solution is instilled in 2.2 g of the polymer described in example 4c, which is introduced suspended in 25 ml of methanol/$H_2O$ (5:1) and allowed to stir for 3 days at room temperature. Then, it is concentrated by evaporation in a vacuum, stirred up with diethyl ether, decanted from precipitated oil, the remaining residue is dissolved in 20 ml of 1N NaOH and saponified for 3 hours at room temperature. Then, it is neutralized with dilute HCl and the solution is desalted by an Amicon-ultrafiltration membrane YM5 and finally freeze-dried.

Yield: 2.18 g $H_2O$ content (Karl-Fischer): 6.3% Gd determination (AAS): 15.97% $T_1$ relaxivity ($H_2O$): 11.77±0.29 [l/mmol.sec] $T_1$ relaxivity (plasma): 12.07±0.15 [l/mmol.sec]

Example 7

Gd Complex of $N^5$-{6-[4,7,10-tris-(carboxymethyl)-1,4,7,10-tetraazacyclododecan-1-yl]-5-hydroxy-3-oxa-hexyl}-$N^5$-(2-carboxymethyl)-poly-L-lysine 2.20 g of the polymer described in example 4c is dissolved in 25 ml of $H_2O$ and adjusted to pH 10.0 by adding 1N NaOH. A solution of 2.6 g (22 mmol) of sodium-chloroacetate in 20 ml of $H_2O$ is instilled slowly in the above at 50° C. and the pH is kept at 10 by adding NaOH. After completion of the addition, it is stirred overnight at this temperature, then neutralized with dilute hydrochloric acid and the solution is desalted by an Amicon-ultrafiltration membrane YM5. After freeze-drying, 2.27 g of flocculent powder is obtained.

$H_2O$ content (Karl-Fischer): 8.3% Gd determination (AAS): 16.40% $T_1$ relaxivity ($H_2O$): 12.13±0.19 [l/mmol.sec] $T_1$ relaxivity (plasma): 13.29±0.34 [l/mmol.sec]

Example 8

Gd Complex of $N^5$-{6-[4,7,10-tris-(carboxymethyl)-1,4,7,10-tetraazacyclododecan-1-yl]-5-hydroxy-3-oxahexyl}-$N^5$-(carboxymethoxyacetyl)-poly-L-lysine 2.20 g of the polymer described in example 4c is dissolved in 25 ml of $H_2O$ and adjusted to pH 8.5 by adding 1N NaOH. 1.04 g (9 mmol) of diglycolic acid anhydride (Fluka) is added to this in portions in solid form, and the pH is simultaneously held between 8 and 9 by adding 1N NaOH. After completion of the addition, it is stirred for 15 more minutes, neutralized with dilute hydrochloric acid, ultrafiltered (Amicon YM5) and finally freeze-dried.

Yield: 2.37 g $H_2O$ content (Karl-Fischer): 6.7% Gd determination (AAS): 14.93% $T_1$ relaxivity ($H_2O$): 13.05±0.37 [l/mmol.sec] $T_1$ relaxivity (plasma): 12.95±0.18 [l/mmol.sec]

Example 9

Thioureido conjugate of the Gd complex of $N^5$-{6-[4,7,10-tris-(carboxymethyl)-1,4,7,10-tetraazacyclododecan-1-yl]-5-hydroxy-3-oxa-hexyl}-poly-L-lysine with the Gd complex of 10-(6-isothiocyanato-2-hydroxy-4-oxahexyl)-1,4,7-tris(carboxymethyl)-1,4,7,10-tetraazacyclododecane 2.20 g of the polymer described in example 4c is dissolved in 25 ml of $H_2O$. 3.09 g (4.7 mmol) of the isothiocyanate-Gd complex described in example 2e is added to this under nitrogen in portions in solid form and stirred overnight at room temperature. After ultrafiltration (Amicon YM5), the conductivity of the solution is adjusted to a minimum by ion exchanger (Amberlite IR 120, $H^+$ form, IRA 410, OH form). It is filtered off from the exchanger and freeze-dried.

Yield: 3.43 g $H_2O$ content (Karl-Fischer): 8.1% Gd determination (AAS): 18.47% $T_1$ relaxivity ($H_2O$): 13.79±0.25 [l/mmol.sec] $T_1$ relaxivity (plasma): 14.51±0.13 [l/mmol.sec]

Example 10 a) 10-(2,3,4-Trihydroxybutyl)-1,4,7-triscarboxymethyl-1,4,7,10-tetraazacyclododecane 10.0 g (28.87 mmol) of 1,4,7-triscarboxymethyl-1,4,7,10-tetraazacyclododecane (DO3A) is dissolved in 40 ml of water and the pH is adjusted to 13 with 5N sodium hydroxide solution. A solution of 6.24 g (43.30 mmol) of 2-(2,2-dimethyl-1,3-dioxolan-4-yl)-ethyleneoxide (DE 3 150 917) in 10 ml of dioxane is added and stirred for 24 hours at room temperature. It is diluted with 60 ml of water and extracted three times with 50 ml of ether. The aqueous phase is brought to pH 2 with 10% hydrochloric acid and is concentrated by evaporation. The residue is dissolved in some water and poured on a cation exchange column (IR 120). After flushing with water, the ligand is eluted with 0.5N aqueous ammonia solution. The fractions are concentrated by evaporation, the ammonium salt is taken up with a little water and poured on an anion exchange column (IRA 67). It is washed first with water and then eluted with 0.5N aqueous formic acid. It is concentrated by evaporation in a vacuum, the residue is dissolved in a little hot methanol and acetone is added, and the title compound crystallizes out.

Yield: 11.31 g (87% of theory) of a white hygroscopic powder $H_2O$ content (Karl-Fischer): 11.1% ; Analysis (relative to anhydrous substance): C 47.99 H 7.61 N 12.44 Cld. C 47.93 H 7.67 N 12.40 b) Gadolinium complex of 10-(2,3,4-trihydroxybutyl)-1,4,7-triscarboxymethyl-1,4,7,10-tetraazacyclododecane 10.0 g (22.2 mmol) of the compound obtained according to example 10a is dissolved in 60 ml of deionized water and 4.02 g (11.1 mmol) of gadolinium oxide is added. It is heated for 3 hours to 90° C. The cooled solution is stirred with 2 ml of acid ion exchanger (IR 120) and 2 ml of basic exchanger (IRA 410) each for 1 hour at room temperature. It is filtered off from the exchanger and the filtrate is boiled up briefly with activated carbon. After filtering and freeze-drying, a white, amorphous powder is obtained.

Yield: 12.76 g (95% of theory) $H_2O$ content (Karl-Fischer): 12.3% Analysis (relative to anhydrous substance): C 35.73 H 5.17 Gd 25.99 N 9.26 Cld. C 35.68 H 5.24 Gd 25.93 N 9.21 c) Gd Complex of $N^5$-{3-[4,7,10-tris(carboxymethyl)-1,4,7, 10-tetraazacyclododecan-1-yl]-2-hydroxy-propyl}-poly-L-lysine 13.8 g (20 mmol) of the Gd complex of example lob is dissolved in 120 ml of methanol, mixed with 4.28 g (20 mmol) of $NaIO_4$ and stirred up for 4 hours with exclusion of light. Then, it is filtered off from insolubles and the filtrate is freeze-dried. The lyophilizate is dissolved in as little water as possible and reprecipitated with ethanol/ether (3:1). The precipitate is suctioned off, dissolved with 2.47 g (15 mmol) of poly-L-lysine-hydrochloride in 350 ml of buffer of pH 9.0 (Riedel de Haën, borax/HCl) and, after adding 3.78 g (60 mmol) of sodium cyanoborohydride, it is stirred for 6 days at room temperature with exclusion of light. The solution is then ultrafiltered (AMICON YM5-membrane) and then freeze-dried.

Yield: 7.29 g (71% of theory) $H_2O$ content (Karl-Fischer): 3.1% Gd determination (AAS): 15.98% $T_1$ relaxivity ($H_2O$): 12.33±0.19 [l/mmol.sec] $T_1$ relaxivity (plasma): 12.75±0.08 [l/mmol.sec]

Example 11

Gd Complex of $N^5$-{3-[4,7,10-tris(carboxymethyl)-1,4,7, 10-tetraazacyclododecan-1-yl]-2-hydroxypropyl}-$N^5$-(Carboxymethoxyacetyl)-poly-L-lysine 1.7 g of the polymer described in example 10c is dissolved in 20 ml of $H_2O$ and adjusted to pH 8.5 by adding 1N NaOH. 772 mg (6 mmol) of diglycolic acid anhydride (Fluka) is added in portions to this with stirring, and the pH is kept between pH 8.0 and 9.0 by adding 1N NaOH. After completion of the addition, it is stirred for 15 more minutes, neutralized with dilute hydrochloric acid, ultrafiltered (AMICON YM5) and finally freeze-dried.

Yield: 1.90 g $H_2O$ content (Karl-Fischer): 7.3% Gd determination (AAS): 14.79% $T_1$ relaxivity ($H_2O$): 12.39±0.35 [l/mmol.sec] $T_1$ relaxivity (plasma): 13.18±0.21 [l/mmol.sec]

Example 12 a) 2,3-Epoxy-1-[4-(2-ethoxycarbonylethyl)-phenoxy]-propane 3.56 g (148.5 mmol) of sodium hydride is added to 24.03 g (123.74 mmol) of 2-(4-hydroxyphenyl)-propanoic acid ethyl ester in 400 ml of dimethylformamide and stirred for 1 hour at room temperature (under nitrogen). 34.35 g (371.22 mmol) of epichlorohydrin is added and then heated for 24 hours at 70° C. It is cooled in an ice bath to 0° C. and 800 ml of water is carefully added. Then, it is extracted twice with 350 ml of ether each. The combined ether phases are washed once with 300 ml of water, dried on magnesium sulfate and concentrated by evaporation in a vacuum. The residue is chromatographed on silica gel (mobile solvent: hexane/ethyl acetate=20:1)

Yield: 20.75 g (67% of theory) of a colorless oil; Analysis (relative to anhydrous substance): C 67.18 H 7.25 Cld. C 67.09 H 7.32 b) 10-[2-Hydroxy-3-(4-(2-carboxyethyl)-phenoxy)-propyl]-1,4,7-tris(carboxymethyl)-1,4,7,10-tetraazacyclododecane 10 g (28.87 mmol) of 1,4,7-triscarboxymethyl-1,4,7,10-tetraazacyclododecane (=DO3A) and 12.99 g (51.96 mmol) of 2,3-epoxy-1-[4-(2-ethoxycarbonylethyl)-phenoxy]-propane are added to 80 ml of dioxane/60 ml of water and adjusted to pH 14 with 6N potassium hydroxide solution. It is stirred for 12 hours at room temperature. Then, it is refluxed for 2 hours. It is adjusted to pH 7 with 5N hydrochloric acid and evaporated to dryness in a vacuum. The residue is absorptively precipitated in 200 ml of ethanol/50 ml of chloroform at 60° C. The precipitated potassium chloride is filtered off and the filtrate is concentrated by evaporation in a vacuum. The residue is purified on a reversed phase column (RP-18, washing with water, then elution with tetrahydrofuran/water=2:1). The main fractions are concentrated by evaporation in a vacuum.

Yield: 7.88 g (48% of theory) of a vitreous solid; Analysis (relative to anhydrous substance): C 54.92 H 7.09 N 9.85 Cld. C 54.87 H 7.15 N 9.79 c) Gadolinium complex of 10-[2-hydroxy-3-(4-(2-carboxyethyl)-phenoxy)-propyl]-1,4,7-tris(carboxymethyl)-1,4,7,10-tetraazacyclododecane 7.5 g (13.19 mmol) of the title compound of example 21b is dissolved in 50 ml of deionized water and 2.39 g (6.59 mmol) of gadolinium oxide is added. It is heated for 3 hours to 90 ° C. The cooled solution is stirred for one hour with 7 ml of weakly acid ion exchanger (AMB 252 c) at room temperature. It is filtered off and freeze-dried.

Yield: 8.96% (94% of theory) of a colorless, amorphous powder; Analysis (relative to anhydrous substance): C 43.20 H 5.16 N 7.75 Gd 21.75 Cld. C 43.13 H 5.29 N 7.86 Gd 21.53 d) Gd Complex of $N^5$-{3-[4-(3-(4,7,10-tris-carboxymethyl-1,4,7,10-tetraaza-cyclododecan-1-yl)-2-hydroxypropoxy)-phenyl]-propionyl}-poly-L-lysine 10.84 g (15 mmol) of the complex acid described in example 12c is dissolved in 50 ml of DMF/$H_2O$ (1:1), mixed with 6.68 g (15 mmol) of N-cyclohexyl-N'-(2-morpholinoethyl)-carbodiimide metho-p-toluenesulfonate [Aldrich] and added to a solution of 2.09 g (10 mmol) of poly-L-lysine-hydrobromide released to the amine analogously to example 11. The reaction mixture is stirred for 24 hours at room temperature, freed by an ultrafiltration (AMICON YM5-membrane) of low-molecular substances and the retentate is freeze-dried.

Yield: 5.98 g (74% of theory) $H_2O$ content (Karl-Fischer): 6.39% Gd determination (AAS): 17.13% $T_1$ relaxivity (H.0): 12.73±0.45 [l/mmol.sec] $T_1$ relaxivity (plasma): 14.51±0.22 [l/mmol.sec]

Example 13

Indium-(111)-labeled Gd complex of $N^5$-{6-[4,7,10-tris-(carboxymethyl)-1,4,7,10-tetraazacyclododecan-1-yl]-5-hydroxy-3-oxahexyl}-$N^5$-(carboxymethoxyacetyl)-poly-L-lysine 1 mg of the title compound of example 8 in 150 µl of water (pH 4.0/hydrochloric acid) is mixed with 30 µl of an indium(111) chloride solution (50 mCi/mil in 0.05M hydrochloric acid) and kept at 50° C. for 3 hours. Then, it is brought to pH 6 with 0.01N of sodium hydroxide solution and 6 µl of a 0.01M di-sodium-EDTA solution is added (to bind free In and Gd). The thus labeled polymer complex is purified by exclusion chromatography (HPLC/TSK-400/buffer MES. Cl, pH 6.2) and can be used for radiodiagnostic tests.

Example 14

Yttrium(90)-labeled Gd complex of $N^5$-{6-[4,7,10-tris-(carboxymethyl)-1,4,7,10-tetraazacyclododecan-1-yl]-5-hydroxy-3-oxahexyl}-$N^5$-(carboxymethoxyacetyl)-poly-L-lysine In an analogous way (see example 13), a Y-(90)-polymer complex of the title compound of example 8 suitable for radiotherapy can be produced if yttrium(90)chloride is used instead of In(111) chloride.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A polymeric compound of formula I $$(M)_n A \qquad (I)$$

in which

M is a radical of a macrocyclic complexing agent,

A is a polymeric backbone molecule having a deficit of m amino groups, m hydroxy groups and/or m carboxy groups, which prior to bonding to $(M)_n$ are present in A, said deficit resulting from the bonding of $(M)_n$ to A via X groups of $(M)_n$, n is a number 1 to 400, each m independently is 1–400, the sum of all m's being equal to n, each M, independently of one another, is a complexing agent of formula IA

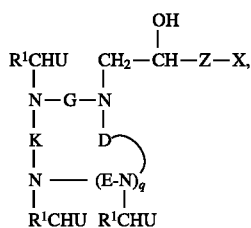

in which

D, E, G and K, can be the same or different, and each is a group —$(CH_2)_o$—, o, in each case, is 2, 3, 4 or 5, q is 0, 1 or 2, $R^1$ is hydrogen, $C_1$–$C_4$ alkyl, phenyl or $C_7$–$C_{12}$ aralkyl, U is $CO_2H$ or $PO_3H_2$, Z is —$CH_2$—O—$C_6H_4$—$CH_2$—$CH_2$—, —$CH_2$—O—$CH_2$—$CH_2$—O—$CH_2$—$CH_2$—, —$CH_2$—O—$C_6H_4$—, —$CH_2$—O— —$CH_2$—CH(OH)—$CH_2$—O—$CH_2$—$CH_2$—, —$CH_2$—O—$CH_2$—CH(COOH)—$CH_2$—O—$CH_2$—$CH_2$—,

—$CH_2$—O—$C_6H_3$—$CH_2$—,
          |
         $OCH_3$

—$CH_2$—O—$C_6H_3$—,
          |
         COOH

—$CH_2$—O—$C_6H_4$—O—$CH_2$—$CH_2$—,

—$CH_2$—O—$CH_2$—$CH_2$—, —$CH_2$—, —$(CH_2)_2$—, —$(CH_2)_3$—, —$(CH_2)_4$—, —$CH_2$—O—$C_6H_4$—O—$CH_2$—$CH_2$—O—$CH_2$—,

—$CH_2$—O—CH—$CH_2$—,
          |
         $CH_2$—COOH

—$CH_2$—O—$CH_2$—CH—$CH_2$—,
               |
              $CH_2$—COOH

—$CH_2$—O—$CH_2$—CH—,
               |
              $CH_2$—COOH

—$CH_2$—O—$CH_2$—$CH_2$—O—$CH_2$—$CH_2$—O—$CH_2$—$CH_2$, —$CH_2$—O—$CH_2$—$C_6H_4$—$CH_2$—, —$CH_2$—O—$C_6H_4$—$CH_2$—$CH_2$—O—$CH_2$—$CH_2$—, —$CH_2$—O—$C_6H_4$—$CH_2$—O—$CH_2$$CH_2$—, —$C_6H_4$—, —$C_6H_4$—O—$CH_2$$CH_2$— or —$C_6H_4$—$CH_2$—,

X is —CONH—, —NHCO—, —NHCS—, —NHCSNH—, —NHCONH—, —$CO_2$—, —O—, —OCO—, —$COCH_2O$—, —$NR^2CH_2CONH$—, —$NR^2CH_2COO$—, —$OCHR^2$—CONH—, —$OCHR^2COO$— or

—NR—, $R^2$ is hydrogen or —$(CH_2)_p COOH$, p is 1–5,

R is hydrogen, a $C_1$–$C_{20}$ hydrocarbon radical optionally substituted by 1 to 3 carboxy, 1 to 3 sulfonic acid, 1 to 5 hydroxy, 1 to 5 $C_1$–$C_{10}$ alkoxy, 1 to 5 $C_6$–$C_{10}$ aryloxy, 1 to 5 $C_7$–$C_{11}$ aralkoxy, 1 to 5 ester and/or 1 to 5 amide groups, and/or optionally containing 1 to 3 carbonyl, 1 to 3 ester, 1 to 3 amide and/or 1 sulfonyl groups and/or 1 to 10 oxygen and/or 1 to 4 nitrogen atoms, or a second molecule IA, which is the same as or different from the first;

a completely or incompletely metalated complex thereof with element(s) of atomic numbers 21–29, 31, 32, 37–39, 42–44, 49 or 57–83; or a pharmaceutically acceptable salt of said polymeric compound or of said metalated complex.

2. A compound according to claim 1, wherein A is a polypeptide, polyallylamine, poly methacrylamide or polyaminocarbohydrate.

3. A compound according to claim 1, wherein A is polylysine having a deficit of n amino groups.

4. A compound according to claim 1, wherein said compound is a metalated complex containing complexed ions of an element of atomic number 21–29, 39, 42, 44 or 57–83.

5. A compound according to claim 1, wherein said compound is a metalated complex containing complexed radioisotopes of an element of atomic number 27, 29, 31, 32, 37–39, 43, 49, 62, 64, 70, 75 or 77.

6. A compound according to claim 1, wherein n is 1 to 10.

7. A compound according to claim 1, wherein n is 10 to 200.

8. A compound according to claim 1, wherein macrocyclic complexing agent M is 1,4,7,10-tetraazacyclododecane-1,4,7-triacetic acid, 1,4,7-triazacyclononane-1,4-diacetic acid, 1,4,8,11-tetraazatetradecane-1,4,8-triacetic acid, or 1,5,9- triazacyclododecane-1,5-diacetic acid, each bonded to A via —CH$_2$—CH(OH)—Z—X.

9. A method of obtaining an MRI image comprising administering a compound of claim 1 to a patient and imaging said patient.

10. A method of obtaining an X-ray image comprising administering a compound of claim 1 to a patient and imaging said patient.

11. A method of obtaining a radiotherapy image comprising administering a compound of claim 1 to a patient and imaging said patient.

12. A method of radiotherapy comprising administering to a patient an effective amount of a compound of claim 1 comprising a radioactive ion.

13. A pharmaceutical composition comprising a physiologically compatible compound according to claim 1 and a pharmaceutically acceptable carrier.

14. A process for the production of compounds of general formula I $$(M)_nA \quad (I)$$

in which

M is a radical of a macrocyclic complexing agent,

A is a polymeric backbone molecule having a deficit of m amino groups, m hydroxy groups and/or m carboxy groups, which prior to bonding to $(M)_n$ are present in A, n is a number 1 to 400, each m independently is 1–400, the sum of all m's being equal to n, each M, independently of one another, is a complexing agent of formula IA

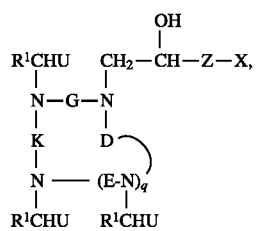

in which

D, E, G and K, can be the same or different, and each is a group —(CH$_2$)$_o$— with o being 2, 3, 4 or 5 q is 0, 1 or 2, $R^1$ is hydrogen, $C_1$–$C_4$ alkyl, phenyl or $C_7$–$C_{12}$ aralkyl, U is CO$_2$H or PO$_3$H$_2$, Z is a straight-chain, branched, saturated or unsaturated $C_1$–$C_{20}$ alkylene group, optionally containing imino, phenylene, phenylenoxy, phenylenimino, amido, hydrazido, carbonyl or ester groups and/or oxygen, sulfur and/or nitrogen atoms and/or optionally substituted by hydroxy, mercapto, oxo, thioxo, carboxy, ester and/or amino, X is —CONH—, —NHCO—, —NHCS—, —NHCSNH—, —NHCONH—, —CO$_2$—, —O—, —OCO—, —COCH$_2$O—, —NR$^2$CH$_2$CONH—, —NR$^2$CH$_2$COO—, —OCHR$^2$CONH—, —OCHR$^2$COO— or —NR—

$R^2$ is hydrogen or —(CH$_2$)$_p$COOH with p being 1–5,

R is hydrogen, a $C_1$–$C_{20}$ hydrocarbon radical optionally substituted by 1 to 3 carboxy, 1 to 3 sulfonic acid, 1 to 5 hydroxy, 1 to 5 $C_1$–$C_{10}$ alkoxy, 1 to 5 $C_6$–$C_{10}$ aryloxy, 1 to 5 $C_7$–$C_{11}$ aralkoxy, 1 to 5 ester and/or 1 to 5 amide groups, and/or optionally containing 1 to 3 carbonyl, 1 to 3 ester, 1 to 3 amide and/or 1 sulfonyl groups and/or 1 to 10 oxygen and/or 1 to 4 nitrogen atoms, or a second molecule IA, which is the same as or different from the first, a completely or incompletely metalated complex thereof with element(s) of atomic numbers 21–29, 31, 32, 37–39, 42–44, 49 or 57–83, or a pharmaceutically acceptable salt thereof.

wherein n molecules of general formula IA'

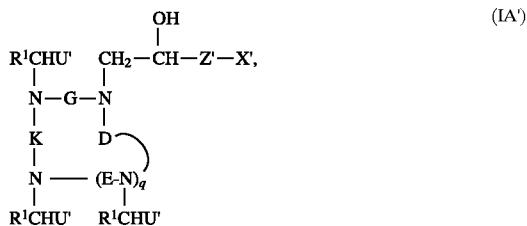

in which

Z' stands for Z or a direct bond,

U' stands for a CO$_2$Y or PO$_3$HY group with Y meaning a hydrogen atom, a metal ion equivalent of an element of atomic numbers 21–29, 31, 32, 37–39, 42–44 or 57–83 or an acid protecting group, X' stands for a C*O, NH$_2$, NCS, NCO, OFu, Hal,

COCH$_2$Hal, CHO and anhydride group with C*O meaning an activated carbonyl group, Fu meaning a leaving group or a hydrogen atom and Hal meaning a fluorine, chlorine, bromine or iodine atom, are reacted with a backbone molecule A', which contains at least n amino, n hydroxy or n carboxy groups, then are optionally reduced and optionally are reacted with a reactant introducing substituent R, then optionally the acid protecting groups are removed and optionally reacted with at least one metal oxide or metal salt of an element of atomic numbers 21–29, 31, 32, 37–39, 42–44 or 37–83 (and the metal complexing also can take place before the introduction of substituent R) and optionally then still present acidic hydrogen atoms are completely or partially substituted by cations of inorganic and/or organic bases, amino acids or amino acid amides.

15. A process for the production of the pharmaceutical agents according to claim 13, wherein the polymer complex dissolved or suspended in water or physiological salt solution, optionally with the additives usual in galenicals, is brought into a form suitable for enteral or parental administration.

16. A compound according to claim 1, wherein o is, in each case, 2 or 3.

17. A compound according to claim 1, wherein $R^1$ is H, methyl, ethyl or benzyl.

18. A compound according to claim 1, wherein group R is —CH$_2$COOH, —(CH$_2$)$_2$COOH, —CH(COOH)CH$_2$COOH, —CH$_2$—CH(COOH)CH$_2$OH, —CH$_2$SO$_3$H, —(CH$_2$)$_2$SO$_3$H, —COCH$_3$, —COCH$_2$OH, —COCHOHCH$_2$OH, —COCH$_2$O-CH$_2$COOH, —CO(CHOH)$_4$CH$_2$OH, —COCH$_2$COOH, —CO(CH$_2$)$_2$COOH, —CO(CH$_2$)$_3$COOH, —CO(CH$_2$)$_4$COOH, —COCHOHCOOH, —CO(CHOH)$_2$COOH, —COCH$_2$CHOHCH$_2$COOH, —SO$_2$CH$_2$COOH, —SO$_2$(CH$_2$)$_2$COOH, —SO$_2$CH$_3$, —CO—CH$_2$—CH$_2$—CO—NH—CH$_2$—CONH—CH$_2$—COOH, —CO—CH$_2$—CH$_2$—CO—O—C$_2$H$_5$, —CO—CH$_2$—CH$_2$COO—CH$_2$—C$_6$H$_5$, —CO—CH$_2$—O—CH$_2$—CH$_2$—O—CH$_2$—CH$_2$—OCH$_3$, —CO—CH$_2$—C$_6$H$_4$—O—CH$_2$—CH$_2$—O—CH$_2$—CH$_2$—OCH$_3$, —CO—CH$_2$—CH$_2$—CONH—C$_6$H$_4$—O—CO—CH$_2$—O—CO—C$_7$H$_{15}$, —CO—C$_6$H$_4$—O—CO—C$_5$H$_{11}$, —CO—CH$_2$—CH$_2$—(CH$_2$)$_8$—CO—CH$_2$—CH$_2$—CONH—CH(CH$_3$)—COOH, —COCH$_2$CH$_2$—COO—CH(CH$_3$)—CH$_2$—NHCO—CH$_2$OH,

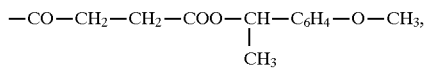

—SO$_2$—CH$_2$—CH$_2$—CH$_2$—CH$_2$—CH$_2$—CH$_3$, —SO$_2$—C$_6$H$_4$—COOH, —CO—CH$_2$—O—CH$_2$—CH$_2$—O—CH$_2$—CH$_2$—OCH$_3$, —CO—CH$_2$—NH—CO—CH$_2$—O—CH$_2$—CH$_2$—OCH$_3$, —CO—C$_6$H$_4$—COO— —CH$_2$—CH$_3$ or —CO—CH$_2$—CH$_2$—COO—CH$_2$—CH$_2$—OCO—CH$_2$—CH$_2$—CONH—CH$_2$—CONH—C$_6$H$_5$.

19. A method according to claim 9, wherein said compound is administered in an amount of 0.0001–5 mmole/kg.

20. A method according to claim 10, wherein said compound is administered in an amount of 0.1 μmol/kg.–5 μmmol/kg.

21. A composition according to claim 13, wherein said composition contains 0.1 μmole–3 mole/liter of said compound.

22. A compound according to claim 1, wherein said compound is:

a thioureido conjugate of Gd complex of 10-(3-isothiocyanato-2-hydroxypropyl)-1,4,7-triscarboxymethyl-1,4,7,10-tetraazacyclododecane with poly-L-lysine;

a thioureido conjugate of Gd complex of 10-(6-isothiocyanato-2-hydroxy-4-oxahexyl)-1,4,7-triscarboxymethyl-1,4,7,10-tetraazacyclododecane with poly-L-lysine;

a thioureido conjugate of Gd complex of 10-(9-isothiocyanato-2-hydroxy-4,7-dioxanonyl)-1,4,7-triscarboxymethyl-1,4,7,10-tetraazacyclododecane with poly-L-lysine;

a Gd complex of N$^5$-{6-[4,7,10-tris-(carboxymethyl)-1,4,7,10-tetraazacyclododecan-1-yl]-5-hydroxy-3-oxahexyl}-poly-L-lysine;

a Gd complex of N$^5$-{6-[4,7,10-tris-(carboxymethyl)-1,4,7,10-tetraazacyclododecan-1-yl]-5-hydroxy-3-oxahexyl}-N$^5$-(2-carboxyethyl)-poly-L-lysine;

a Gd complex of N$^5$-{6-[4,7,10-tris-(carboxymethyl)-1,4,7,10-tetraazacyclododecan-1-yl]-5-hydroxy-3-oxahexyl}-N$^5$-(2-dicarboxyethyl)-poly-L-lysine;

a Gd complex of N$^5$-{6-[4,7,10-tris-(carboxymethyl)-1,4,7,10-tetraazacyclododecan-1-yl]-5-hydroxy-3-oxahexyl}-N$^5$-(2-carboxymethyl)-poly-L-lysine;

a Gd complex of N$^5$-{6-[4,7,10-tris-(carboxymethyl)-1,4,7,10-tetraazacyclododecan-1-yl]-5-hydroxy-3-oxahexyl}-N$^5$-(carboxymethoxyacetyl)-poly-L-lysine;

a thioureido conjugate of Gd complex of N$^5$-{6-[4,7,10-tris-(carboxymethyl)-1,4,7,10-tetraazacyclododecan-1-yl]-5-hydroxy-3-oxa-hexyl}-poly-L-lysine with the Gd complex of 10-(6-isothiocyanato-2-hydroxy-4-oxahexyl)-1,4,7-tris(carboxymethyl)-1,4,7,10-tetraazacyclododecane;

a Gd complex of N$^5$-{3-[4,7,10-tris(carboxymethyl)-1,4,7,10-tetraazacyclododecan-1-yl]-2-hydroxy-propyl}-poly-L-lysine;

a Gd complex of N$^5$-{3-[4,7,10-tris(carboxymethyl)-1,4,7,10-tetraazacyclododecan-1-yl]-2-hydroxypropyl}-N$^5$-(carboxymethoxyacetyl)-poly-L-lysine; or a Gd complex of N$^5$-{3-[4-(3-(4,7,10-tris-carboxymethyl-1,4,7,10-tetraazacyclododecan-1-yl)-2-hydroxypropoxy)phenyl]-propionyl}-poly-L-lysine.

23. A polymeric compound of formula I $$(M)_n A \qquad (I)$$

in which

M is a radical of a macrocyclic complexing agent,

A is a polymeric backbone molecule having a deficit of m amino groups, m hydroxy groups and/or m carboxy groups, which prior to bonding to (M)$_n$ are present in A, said deficit resulting from the bonding of (M) to A via X groups of (M)$_n$, n is a number 1 to 400, each m independently is 1–400, the sum of all m's being equal to n, each M, independently of one another, is a complexing agent of formula IA

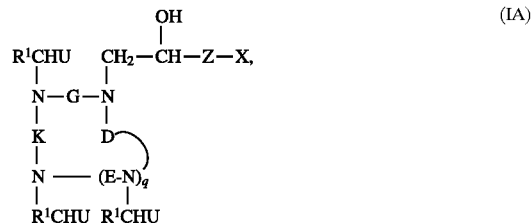

in which

D, E, G and K, can be the same or different, and each is a group —(CH$_2$)$_o$—, o, in each case, is 2, 3, 4 or 5, q is 0, 1 or 2, R$^1$ is hydrogen, C$_1$–C$_4$ alkyl, phenyl or C$_7$–C$_{12}$ aralkyl, U is CO$_2$H or PO$_3$H$_2$, Z is a straight-chain, branched, saturated or unsaturated C$_{1-20}$-alkylene group containing at least one oxygen atom, optionally containing imino, phenylene, phenylenoxy, phenylenimino, amido, hydrazido, carbonyl or ester groups and/or nitrogen atoms and/or optionally substituted by hydroxy, mercapto, oxo, thioxo, carboxy, ester and/or amino, X is —CONH—, —NHCO—, —NHCS—, —NHCSNH—, —NHCONH—, —CO$_2$—, —O—, —OCO—, —COCH$_2$O—, —NR$^2$CH$_2$CONH—, —NR$^2$CH$_2$COO—, —OCHR$^2$CONH—, —OCHR$^2$COO— or —NR—, R$^2$ is hydrogen or —(CH$_2$)$_p$COOH, p is 1–5, R is hydrogen, a C$_1$–C$_{20}$ hydrocarbon radical optionally substituted by 1 to 3 carboxy, 1 to 3 sulfonic acid, 1 to 5 hydroxy, 1 to 5 C$_1$–C$_{10}$ alkoxy, 1 to 5 C$_6$–C$_{10}$ aryloxy, to aralkoxy, 1 to 5 ester and/or 1 to 5 amide groups, and/or optionally containing 1 to 3 carbonyl, 1 to 3 ester, 1 to 3 amide and/or 1 sulfonyl groups and/or 1 to 10 oxygen and/or 1 to 4 nitrogen atoms, or a second moledule IA, which is the same as or different from the first:

a completely or incompletely metalated complex thereof with element(s) of atomic numbers 21–29, 31, 32, 37–39, 42–44, 49 or 57–83; or a pharmaceutically acceptable salt of said polymeric compound or of said metalated complex.

24. A compound according to claim 1, wherein Z is
—$CH_2$—O—$C_6H_4$—$CH_2$—$CH_2$—, —$CH_2$—O—$CH_2$—$CH_2$—O—$CH_2$—$CH_2$—, —$CH_2$—O—$C_6H_4$—, —$CH_2$—O—$CH_2$—CH(OH)—$CH_2$—O—$CH_2$—$CH_2$—, —$CH_2$—O—$CH_2$—CH(COOH)—$CH_2$—O—$CH_2$—$CH_2$—

—$CH_2$—O—$C_6H_3$(OCH$_3$)—$CH_2$—, —$CH_2$—O—$C_6H_3$(COOH)—,

—$CH_2$—O—$C_6H_4$—O—$CH_2$—$CH_2$—, —$CH_2$—O—$CH_2$—$CH_2$—, —$CH_2$—O—$C_6H_4$—O—$CH_2$—$CH_2$—O—$CH_2$—$CH_2$—,

—$CH_2$—O—CH(CH$_2$—COOH)—$CH_2$—,

—$CH_2$—O—$CH_2$—CH(CH$_2$—COOH)—$CH_2$—,

—$CH_2$—O—$CH_2$—CH(CH$_2$—COOH)—,

—$CH_2$—O—$CH_2$—$CH_2$—O—$CH_2$—$CH_2$—O—$CH_2$—$CH_2$—, —$CH_2$—O—$CH_2$—$C_6H_4$—$CH_2$—, —$CH_2$—O—$C_6H_4$—$CH_2$—$CH_2$—O—$CH_2$—$CH_2$—, —$CH_2$—O—$C_6H_4$—$CH_2$—O—$CH_2$—$CH_2$— or —$C_6H_4$—O—$CH_2$—$CH_2$—.

* * * * *